US011083840B2

(12) United States Patent
Gibson et al.

(10) Patent No.: US 11,083,840 B2
(45) Date of Patent: Aug. 10, 2021

(54) MODULAR FLUID PATH ASSEMBLIES FOR DRUG DELIVERY DEVICES

(71) Applicant: AMGEN INC., Thousand Oaks, CA (US)

(72) Inventors: Scott Robert Gibson, Granada Hills, CA (US); Sudeshna Dutta Ray, Thousand Oaks, CA (US); Daniel Eduardo Groszmann, Belmont, MA (US); Mehran Mojarrad, Thousand Oaks, CA (US); Nathan Thomas Balcom, Vista, CA (US); Alejandro Campillo-Agusti, Simi Valley, CA (US); Alan D. Payne, Escondido, CA (US); Lawrence Scott Ring, Laguna Beach, CA (US)

(73) Assignee: AMGEN INC., Thousand Oaks, CA (US)

( * ) Notice: Subject to any disclaimer, the term of this patent is extended or adjusted under 35 U.S.C. 154(b) by 201 days.

(21) Appl. No.: 15/995,442

(22) Filed: Jun. 1, 2018

(65) Prior Publication Data

US 2019/0365987 A1     Dec. 5, 2019

(51) Int. Cl.
*A61M 5/162*     (2006.01)
*A61M 39/14*     (2006.01)
(Continued)

(52) U.S. Cl.
CPC ............ *A61M 5/162* (2013.01); *A61M 39/14* (2013.01); *A61M 5/145* (2013.01); *A61M 5/321* (2013.01); *A61M 2005/1585* (2013.01)

(58) Field of Classification Search
CPC .................. A61M 5/162; A61M 39/14; A61M 2005/1585; A61M 5/321; A61M 5/145;
(Continued)

(56) References Cited

U.S. PATENT DOCUMENTS

| 2001/0025168 A1 | 9/2001 | Gross et al. |
| 2007/0060904 A1 | 3/2007 | Vedrine et al. |

(Continued)

FOREIGN PATENT DOCUMENTS

| EP | 0820779 A1 | 1/1998 |
| WO | WO-2011/133823 A1 | 10/2011 |

OTHER PUBLICATIONS

International Application No. PCT/US2019/030845, International Search Report and Written Opinion, dated Jul. 22, 2019.

*Primary Examiner* — Theodore J Stigell
*Assistant Examiner* — Daniel Moore
(74) *Attorney, Agent, or Firm* — Marshall, Gerstein & Borun LLP

(57) ABSTRACT

Modular fluid path assemblies are provided that include conduit, coupling, and needle portions of a fluid path fluidly coupled to an outlet of a container. The modular fluid path assemblies further include a needle shield having a tip of the needle embedded therein. So configured, in embodiments, the modular fluid path assemblies can be sterilized, a medicament can be filled in the container, and a stopper inserted in the container so that the pre-sterilized and pre-filled modular fluid path assemblies can have a closed container integrity (CCI) seal.

12 Claims, 18 Drawing Sheets

(51) Int. Cl.
*A61M 5/145* (2006.01)
*A61M 5/32* (2006.01)
*A61M 5/158* (2006.01)

(58) Field of Classification Search
CPC .... A61M 5/14248; A61M 2005/14252; A61M 5/14566; A61M 2005/1581; A61M 39/18; A61M 5/348; A61M 2039/0229
See application file for complete search history.

(56) References Cited

U.S. PATENT DOCUMENTS

| | | | |
|---|---|---|---|
| 2010/0152658 A1* | 6/2010 | Hanson | A61M 5/14248 604/136 |
| 2013/0066274 A1* | 3/2013 | O'Connor | A61M 5/16877 604/151 |
| 2013/0237916 A1* | 9/2013 | Hanson | A61L 2/26 604/151 |
| 2017/0189609 A1* | 7/2017 | Wei | A61M 5/16877 |

* cited by examiner

MODULAR FLUID PATH ASSEMBLIES FOR DRUG DELIVERY DEVICES

FIELD OF THE DISCLOSURE

The present disclosure generally relates to drug delivery devices and, more particularly, to fluid path assemblies for drug delivery devices.

BACKGROUND

Some conventional drug delivery devices can utilize a container prefilled with medicament. In such devices, the container can be connected to a needle insertion mechanism. This configuration occupies a relatively large footprint during sterilization and filling. Further, the container, needle insertion mechanism, and fluid path assemblies can often include complex components that increase particulate risk and residuals from the sterilization process.

SUMMARY

In accordance with a first aspect, a modular fluid path assembly for a drug delivery device is described that includes a container having an interior for storing a medicament and an outlet. The assembly further includes a conduit portion of a fluid path fluidly coupled to the outlet of the container, a coupling portion of the fluid path fluidly coupled to the conduit portion and configured to couple the fluid path to a needle insertion mechanism, and a needle of the fluid path fluidly coupled to the coupling portion. The assembly further includes a needle shield having a tip of the needle embedded therein.

According to some forms, the modular fluid path assembly can further include the medicament disposed within the container and a stopper sealingly disposed within the interior of the container.

According to another form, the coupling portion can be a hub having the needle mounted thereto. The hub includes mounting structure that is configured to couple the hub to the needle insertion mechanism. In one approach, the mounting structure can include a tongue of a tongue-and-groove cooperating structure with the needle insertion mechanism.

According to another form, the assembly can further include a cannula of the fluid path that is configured to operably couple to the needle insertion mechanism to be driven thereby.

Any of the above modular fluid path assemblies can be combined with the needle insertion mechanism, wherein the needle insertion mechanism is a scotch yoke mechanism. In these versions, the hub can be a yoke member of the scotch yoke mechanism or can mount to a yoke member of the scotch yoke mechanism.

According to another form, the needle can provide the conduit and coupling portion, that needle having a proximal end of the needle coupled to the container to be fluidly coupled to the interior and a distal end. In this form, the modular fluid path assembly can further include a septum mounted to the needle and a cannula having a portion extending around the septum and an elongate body extending coaxially along and around the distal end of the needle, where a portion of the septum and cannula are received within an interior cavity of the needle shield.

This form of the modular fluid path assembly can include any of the following aspects. In one embodiment, the modular fluid path assembly can be provided in combination with a carrier having supports configured to engage the modular fluid path assembly to maintain the relative positions of the container, needle, septum, cannula, and needle shield after assembly. In another embodiment, the needle can have a bent configuration including a bend so that the distal end of the needle extends along an axis generally orthogonal to a longitudinal axis of the barrel. In a further embodiment, the modular fluid path assembly with the bent configuration can be provided in combination with a drug delivery device, where the drug delivery device includes a housing, a needle insertion mechanism, and a plunger drive mechanism configured to selectively drive the stopper through the container to thereby force the medicament through the needle and cannula. The bend of the needle can be the coupling portion of the fluid path and a sliding needle member of the needle insertion mechanism can be configured to engage the bend of the needle and drive the needle to insert the tip of the distal end of the needle to a predetermined subcutaneous depth. A sliding cannula member of the needle insertion mechanism can be configured to engage the cannula and insert the cannula to a predetermined subcutaneous depth following the needle, where the sliding needle member is further configured to retract the needle after insertion of the cannula. In one version, the cannula can include an outwardly projecting flange and the sliding cannula member can be configured to engage the outwardly projecting flange and hold the cannula in place during needle shield removal.

In accordance with a second aspect, a method of preparing a modular fluid path assembly for a drug delivery device is described that includes providing a container having an interior for storing a medicament and an outlet, coupling a conduit portion of a fluid path to an outlet of the container, where the fluid path further includes a coupling portion that is configured to couple the fluid path to a needle insertion mechanism and a needle fluidly coupled to the coupling portion. The method can further include embedding a tip of the needle in a needle shield, sterilizing the container, conduit, coupling portion, needle, and needle shield, dispensing a medicament into the container, and inserting a stopper into the interior of the container.

According to one form, the method can further include installing the modular fluid path assembly in a drug delivery device. Installing the modular fluid path assembly in the drug delivery device can include operably coupling the coupling portion of the fluid path to a needle insertion mechanism of the drug delivery device and aligning the container with a plunger drive mechanism of the drug delivery device. In a further form, the coupling portion can be a hub having the needle mounted thereto, and operably coupling the coupling portion of the fluid path to the needle insertion mechanism can include inserting mounting structure of the hub into a slot opening of the needle insertion mechanism. In yet a further form, the needle insertion mechanism can be a scotch yoke mechanism and inserting the mounting structure of the hub into the slot opening of the needle insertion mechanism can further include coupling the hub to a drive pin of the scotch yoke mechanism.

According to another form, the method can further include forming first and second bends in the needle so that a distal end of the needle extends along an axis generally orthogonal to a longitudinal axis of the container. In a further form, the second bend of the needle can be the coupling portion of the fluid path, and the method can include installing the modular fluid path assembly in a drug delivery device, where installing the modular fluid path assembly in the drug delivery device can include coupling the second bend of the needle to a needle insertion mechanism configured to drive the needle to insert a tip to a predetermined subcutaneous depth. In yet a further form, the modular fluid path assembly can include a cannula mounted to the needle and installing the modular fluid path assembly in the drug delivery device can include coupling the cannula to the needle insertion mechanism configured to insert the cannula to a predetermined subcutaneous depth following the needle.

In accordance with a third aspect, a syringe is described herein that includes a barrel that has an interior and a needle that has a proximal end coupled to the barrel to be fluidly coupled to the interior and a distal end. The syringe further includes a septum that is mounted to the needle, a cannula that has a portion that extends around the septum and an elongate body that extends coaxially along and around the distal end of the needle, and a needle shield that has an interior cavity. The syringe is configured so that the needle has a tip of the distal end embedded within the needle shield for a closed container integrity seal, and portions of the septum and cannula are received within the interior cavity of the needle shield.

The syringe can be provided in combination with a carrier that has supports that are configured to engage the syringe to maintain the relative positions of the barrel, needle, septum, cannula, and needle shield after assembly.

According to one form, the septum can be a one-way valve.

According to another form, the syringe can further include a medicament disposed within the interior of the barrel and a stopper received within the interior of the barrel. According to a further form, the needle can have a bent configuration so that the distal end of the needle extends along an axis generally orthogonal to a longitudinal axis of the barrel. The syringe of this form can be disposed within a drug delivery device. With this configuration, the drug delivery device can include a housing, a needle insertion mechanism that is configured to engage the bent configuration of the needle and drive the needle to insert the tip of the distal end of the needle to a predetermined subcutaneous depth, a cannula insertion mechanism that is configured to insert the cannula to a predetermined subcutaneous depth following the needle, where the needle insertion mechanism is further configured to retract the needle after insertion of the cannula, and a plunger drive mechanism that is configured to selectively drive the stopper through the barrel to thereby force the medicament through the needle and cannula.

According to one form, the cannula can include an outwardly projecting flange and the cannula insertion mechanism can be configured to engage the outwardly projecting flange and hold the cannula in place during removal of the needle shield.

According to another form, the needle insertion mechanism and the cannula insertion mechanism can have a common drive. According to a further form, the common drive can include a torsion spring having a thermal release mechanism.

In accordance with a fourth aspect, a method preparing a syringe is described that includes providing a barrel that has an interior and a needle that has a proximal end coupled to the barrel to be fluidly coupled to the interior and a distal end. The method further includes fitting a septum into a rearwardly opening chamber of a cannula, where the septum has a resilient throughbore extending longitudinally therethrough and the throughbore is aligned with a tubular body of the cannula, fitting the cannula, with the septum received within the chamber, into a needle shield, and sliding the needle through the throughbore of the septum and the tubular body of the cannula to a position so that a tip of the distal end is embedded within the needle shield for a closed container integrity seal.

In accordance with a fifth aspect, a method of preparing a syringe is described that includes providing a barrel that has an interior and a needle that has a proximal end coupled to the barrel to be fluidly coupled to the interior and a distal end. The method further includes inserting a needle through a throughbore of a septum so that the septum is spaced from a tip of the distal end of the needle, inserting the needle through a tubular body of a cannula and fitting the septum into a rearwardly facing chamber of the cannula, and inserting the needle, with the cannula and septum coupled thereto, into a needle shield until the tip of the distal end of the needle is embedded within the needle shield for a closed container integrity seal. According to one form, inserting the needle through the throughbore of the septum can include inserting an expansion tube through the throughbore of the septum, expanding the expansion tube so that a diameter of the throughbore is increased, and extracting the expansion tube.

In further accordance with the foregoing third and fourth aspects, the method can further include any one or more of the following.

According to one form, the method can include releasably coupling the syringe to a carrier, where the carrier has supports that are configured to engage the syringe to maintain the relative positions of the barrel, needle, septum, cannula, and needle shield after assembly. The method can also include sterilizing the syringe, filling the barrel with a predetermined amount of medicament, and/or inserting a stopper into the barrel.

According to another form, the method can include bending the needle so that the distal end extends along an axis generally orthogonal to a longitudinal axis of the barrel. Bending can include forming a first bend and a second bend in the needle. In this form, the method can include installing the syringe in a housing of a drug delivery device. Installing the syringe in the housing can includes coupling the needle to a needle insertion mechanism that is configured to engage the second bend of the needle to drive the needle to insert the tip of the distal end of the needle to a predetermined subcutaneous depth, coupling the cannula to a cannula insertion mechanism that is configured to insert the cannula to a predetermined subcutaneous depth following the needle, where the needle insertion mechanism is further configured to retract the needle after insertion of the cannula, and disposing the barrel adjacent to a plunger drive mechanism that is configured to selectively drive the stopper through the barrel to thereby force the medicament through the needle and cannula.

According to further forms, coupling the needle to the needle insertion mechanism can include coupling the needle to a scotch yoke mechanism, coupling the cannula to the cannula insertion mechanism can include coupling the cannula to the scotch yoke mechanism, and coupling the cannula to the cannula insertion mechanism can include coupling an outwardly projecting flange of the cannula to the cannula insertion mechanism to hold the cannula in place during removal of the needle shield.

BRIEF DESCRIPTION OF THE DRAWINGS

It is believed that the disclosure will be more fully understood from the following description taken in conjunction with the accompanying drawings, wherein.

Skilled artisans will appreciate that elements in the figures are illustrated for simplicity and clarity and have not necessarily been drawn to scale. For example, the dimensions and/or relative positioning of some of the elements in the figures may be exaggerated relative to other elements to help to improve understanding of various embodiments of the present invention. Also, common but well-understood elements that are useful or necessary in a commercially feasible embodiment are often not depicted in order to facilitate a less obstructed view of these various embodiments. It will further be appreciated that certain actions and/or steps may be described or depicted in a particular order of occurrence while those skilled in the art will understand that such specificity with respect to sequence is not actually required. It will also be understood that the terms and expressions used herein have the ordinary technical meaning as is accorded to such terms and expressions by persons skilled in the technical field as set forth above except where different specific meanings have otherwise been set forth herein.

DETAILED DESCRIPTION

Modular fluid path assemblies are provided that can be sterilized, filled, and coupled to an insertion mechanism of a suitable drug delivery device. As such, the modular fluid path assemblies described herein have a smaller footprint without the insertion mechanism for storage, filling, and sterilization. Further, the number of non-primary container parts in the fill and sterilization process are reduced aiding in minimizing particulate risk and complexity of sterilization and residuals.

In embodiments, a modular prefilled syringe and primary container and fluid path assembly is provided with an incorporated needle shield, such that the syringe and assembly can be sterilized prior to being disposed within a drug delivery device and maintain sterility until the needle shield is removed by a user prior to injection. This modular configuration also provides for cannula insertion, if desired, and needle insertion and extraction functions within a drug delivery device.

The modular fluid path assemblies described herein include conduit, coupling, and needle portions of a fluid path fluidly coupled to an outlet of a container. The modular fluid path assemblies further include a needle shield having a tip of the needle embedded therein. So configured, in embodiments, the modular fluid path assemblies can be sterilized, a medicament can be filled in the container, and a stopper inserted in the container so that the pre-sterilized and pre-filled modular fluid path assemblies can have a closed container integrity (CCI) seal.

Figure 1:
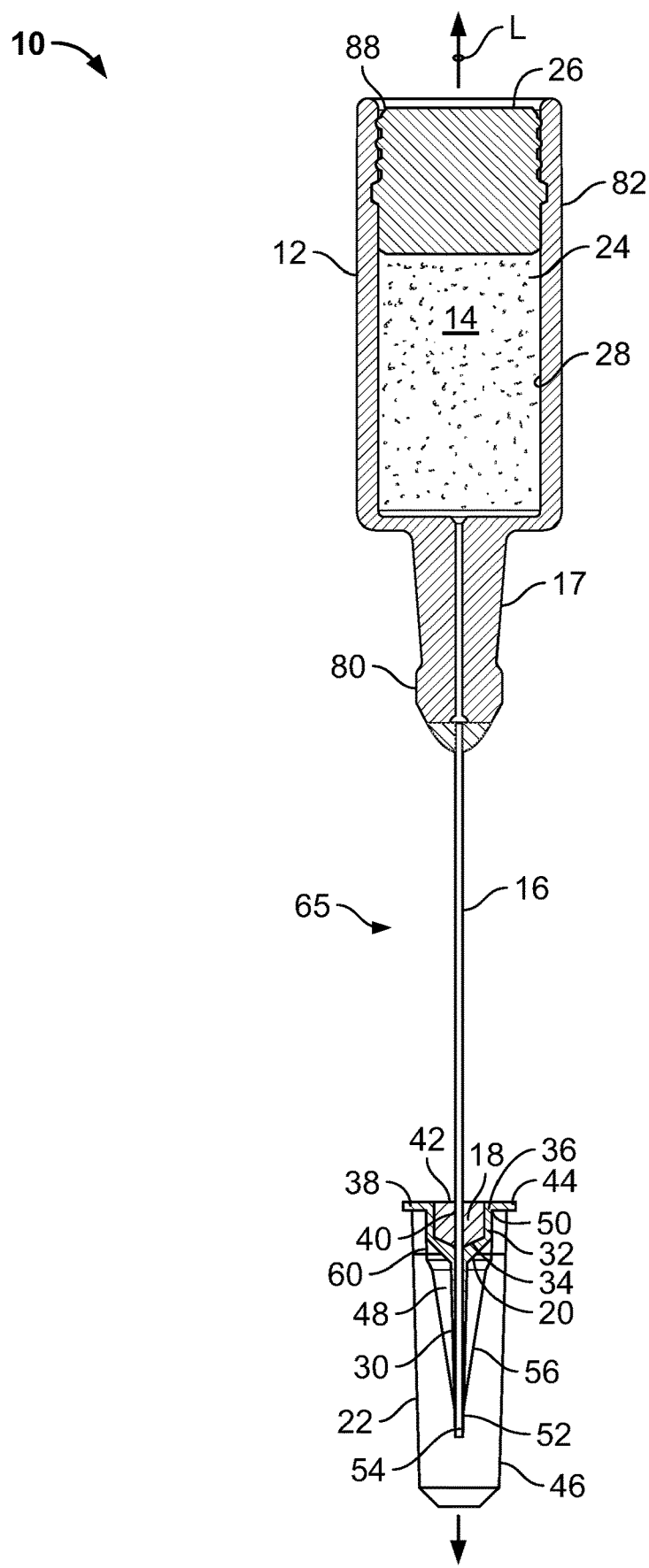
FIG. 1 is a cross-sectional view of one embodiment of a modular fluid path assembly for drug delivery devices.

Details of a modular fluid path assembly in the form of an example prefilled syringe 10 are shown in FIG. 1. The syringe 10 includes a container in the form of a barrel 12 having an interior 14, a needle 16 mounted to the barrel 12 through a needle hub 17 to be fluidly coupled to the interior 14, a septum 18, a cannula 20, and a needle shield 22. In this embodiment, the needle 16 provides the conduit and coupling portion of the fluid path, as set forth in more detail below. The needle 16 may be made of a more rigid material than the cannula 20. For example, the needle 16 may be made of metal, whereas the cannula 20 may be made of plastic. Moreover, the relative flexibility of the cannula 20 may render the cannula 20 suitable for being left inside the patient for several minutes, hours, or days without substantial discomfort to the patient. The barrel 12 can be filled with a suitable medicament 24 and closed off by a stopper 26 inserted into the barrel 12 to sealingly engage an interior surface 28 of the barrel 12. The septum 18 is sized and configured to sealingly engage the needle 16 and the cannula 20 and the cannula sealingly engages the needle shield 22, so that the assembly with the stopper 26 is hermetically sealed.

As shown in FIG. 1, the cannula 20 has a tubular configuration with an elongate forward portion 30 and an annular rear portion 32 defining a cavity 34 with a rear facing opening 36. The cannula rear portion 32 can further include an outwardly projecting flange 38 that extends around the opening 36. The septum 18 has a bore 40 extending longitudinally therethrough and the cavity 34 is sized to receive the septum 18. So configured, with the needle 16 extending through the bore 40 of the septum 18, the septum 18 can be used to mount the cannula 20 to the needle 16. In one form, the cavity 34 and septum 18 are sized so that the septum 18 is fully received within the cavity 34 so that a rear surface 42 of the septum 18 is generally coplanar with a rear surface 44 of the cannula 20.

The needle shield 22 includes a body 46 defining an internal cavity 48 with a rearwardly facing opening 50. The internal cavity 48 has a cylindrical forward portion 52 sized to receive a tip 54 of the needle 16, a conical intermediate portion 56, and a cylindrical rear portion 60 sized to receive the rear portion 32 of the cannula 20.

Figure 2:
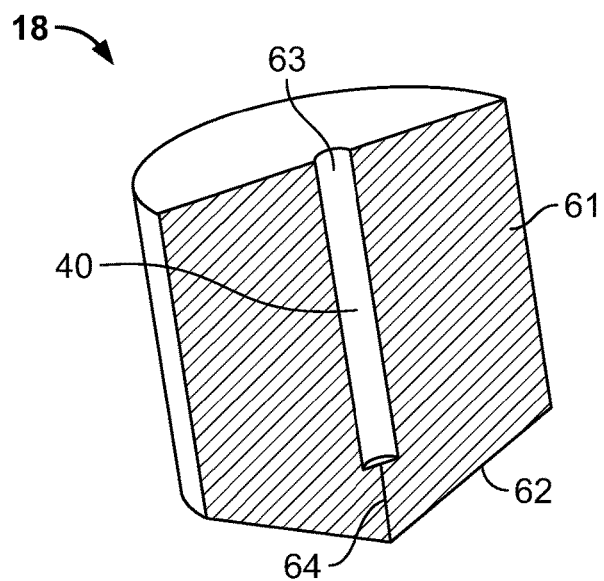
FIG. 2 is a cross-sectional perspective view of one embodiment of a septum for the modular fluid path assembly of FIG. 1.

One example form of a septum 18 is shown in FIG. 2 includes one-way functionalities for the syringe 10 the provide anti-siphon and anti-reflux features. The septum 18 includes a cylindrical body 61 having a conical front surface 62. As discussed above, the bore 40 of the septum 18 extends longitudinally through the body 61. The bore 40 includes an open rear portion 63 having a first diameter and a closed forward portion 64. For example, the closed forward portion 64 can be formed with a slit through the body 61. The body 61 can be made of a resilient material so that it elastically deforms when the member is inserted therethrough and resiliently rebounds so that the body 61 closes the forward portion 64 of the bore 40 when no structure extends therethrough. This configuration allows the septum to act as a one-way valve because fluid entering the bore 40 through the open rear portion 63 can force the closed forward portion 64 open with pressure, while fluid being pressed against the conical front surface 62 forces the body 61 to hold the forward portion 64 tightly closed.

The syringe 10 can be assembled in a number of suitable ways. In a first approach, the septum 18 is pressed into the cavity 34 of the cannula 20. The cannula 20, with the septum 18 received therein, is then inserted into the internal cavity 48 of the needle shield 22 until the flange 38 abuts a rear surface 62 of the needle shield 22. Thereafter, the needle 16 is inserted through the bore 40 of the septum 18, through the elongate forward portion 30 of the cannula 20, and into the forward portion 52 of the internal cavity 48 until the needle tip 54 is embedded into the needle shield body 46 sufficient for a CCI seal.

In a second approach, an expansion tube (not shown) can be inserted through the bore 40 of the septum 18, the needle 18 slid into the expansion tube, and expansion tube extracted from the bore 40 so that the septum 18 is mounted on the needle 18 without the needle 18 damaging the bore 40. The cannula 20 can then be placed on the needle 18 until the needle tip 54 extends through the forward portion 30 and the septum 18 is received within the cavity 34 of the rear portion 32. The needle 16, septum 18, and cannula 20 is then inserted into the internal cavity 44 of the needle shield 22 until the needle tip 54 is embedded into the needle shield body 46 sufficient for a CCI seal.

Regardless of the assembly method, after the septum 18 and cannula 20 are mounted on the needle 16 and the needle 16 embedded in the shield body 46, the syringe 10 can be sterilized, the barrel 12 can be filled with a desired amount of medicament 24, and the stopper 26 can be inserted into the container interior 14. So assembled, a fluid pathway 65 (seen in FIG. 1) for the syringe 10 extending from the stopper 26 within the container interior 14 to the tip 54 of the needle 16 has a CCI seal.

Figure 3:
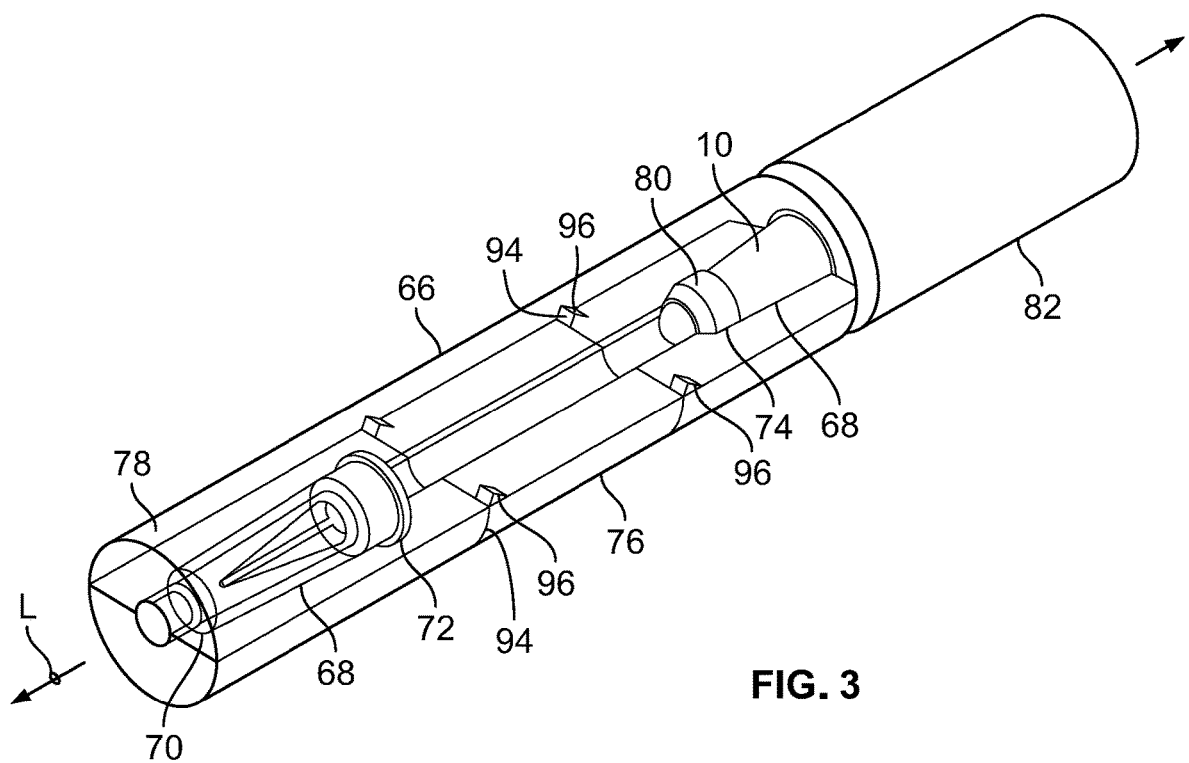
FIG. 3 is a perspective view of one embodiment of a carrier with the modular fluid path assembly of FIG. 1 stored therein.

Turning now to FIG. 3, to preserve the positioning of the components of the syringe 10 and aid in storage, the syringe 10 can mounted within a carrier 66 having supports and/or recesses 68 that engage the syringe 10 to hold the components, including the barrel 12, the needle 16, the septum 18, the cannula 20, and the needle shield 22, relatively stationary with respect to one another so that the seal is maintained. The recesses 68 can include an end wall 70 that abuts the needle shield 22, a slot 72 that receives the outwardly projecting flange 38 of the cannula 20, and a surface 74 to abut a wall of the barrel 12. As shown, the carrier 66 can include a base portion 76 and a cover 78 removably, using fasteners, snap fit, etc., and/or pivotably attached to the base portion 76. The supports and/or recesses 68 can be provided in the base portion 76, the cover 78, or both as desired.

In a first approach, the carrier 66 can be configured to couple to and support a portion of the barrel 12. For example, as shown in FIG. 3, the carrier 66 can couple around the needle hub 17 of the barrel 12 and extend forwardly to support and hold the needle shield 22 and cannula 20 in position. To retain the carrier 66 on the needle hub 17, the hub 17 can include a radially projecting collar 80 and the surface 74 of the recesses 68 can abut the collar 80 to lock the barrel 12 to the carrier 66. Further, the carrier 66 can be sized to abut a main reservoir portion 82 of the barrel 12 when secured to the collar 80. In a second approach, the carrier 66 can be sized with a diameter and length to fully receive the syringe 10. The carrier 66 can have any desired configuration, such as cylindrical as shown, box-shaped, and so forth.

Figure 4:
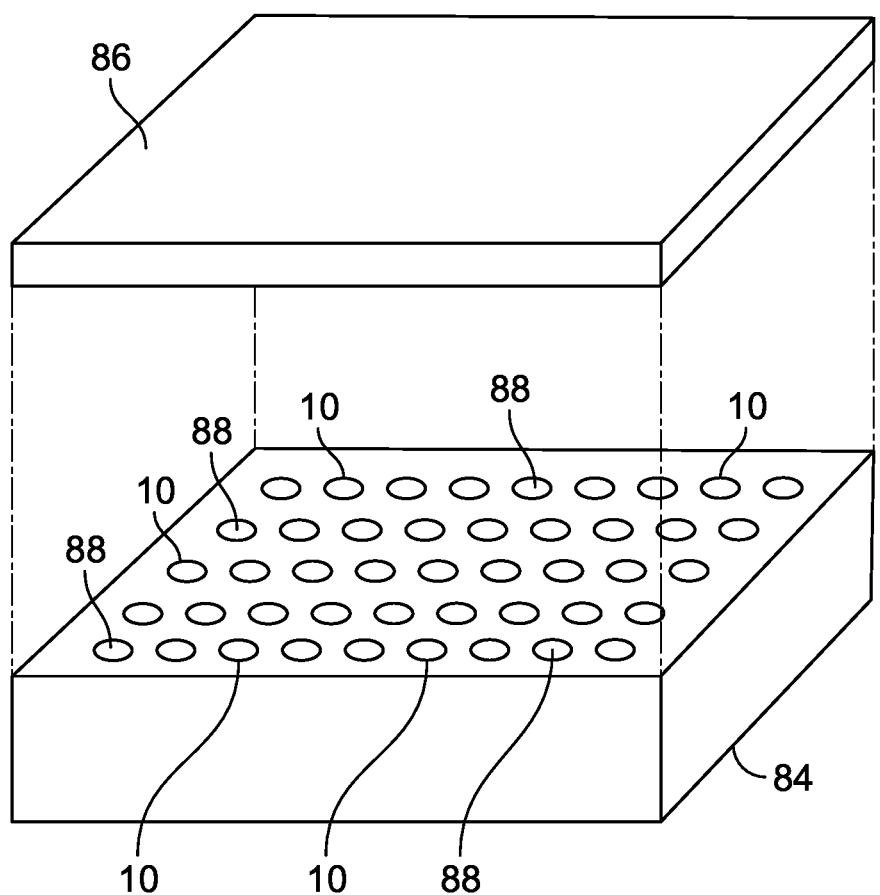
FIG. 4 is a perspective view of one embodiment of a tray and lid for sterilization and filling of modular fluid path assemblies.

After the syringe 10 is secured within the carrier 66, an array of carriers 66 can be placed in a tray 84 for sterilization as shown in FIG. 4. Advantageously, the carriers 66 can be loaded vertically in the tray 84 to maximize the number of carriers 66 that can fit in a given tray. The tray 84 can then be sealed with an Ethylene Oxide (EtO) permeable lid 86 and transported for EtO sterilization with the carriers 66 protecting the components of the syringe 10 from movement throughout the process. After sterilization, the tray 84 can then be allowed to degas.

The sterilized syringes 10 are then suitable for filling with the medicament 24. Advantageously, the carrier 66 that couples to the container collar 80 with the main reservoir portion 82 of the barrel 12 extending rearwardly therefrom can be utilized for efficient filling of the syringe 10. More specifically, the carrier 66 can be positioned within the tray 84 so that an open end 88 of the barrel 12 is exposed upwardly. The medicament 24 can then be deposited into the container interior 14 without removing the syringe 10 from the carrier 66 and without removing both from the tray 84.

By one approach, the tray 84 can be transported to an aseptic filling line that removes the lid 86, fills the syringe barrel 12 with a predetermined quantity of the medicament 24, and then inserts the stopper 26 into the barrel interior 14 to provide a CCI seal for the syringe 10. Further, after filling, the syringe 10 may be subjected to rotary particle inspection and the carrier 66 can continue to provide support to the components of the syringe 10 during the inspection to maintain the relative position and alignment of the components. Finally, the filled syringe 10 may be stored in the carrier 66 until needed for assembly into a drug delivery device, described in more detail below.

Figure 5:
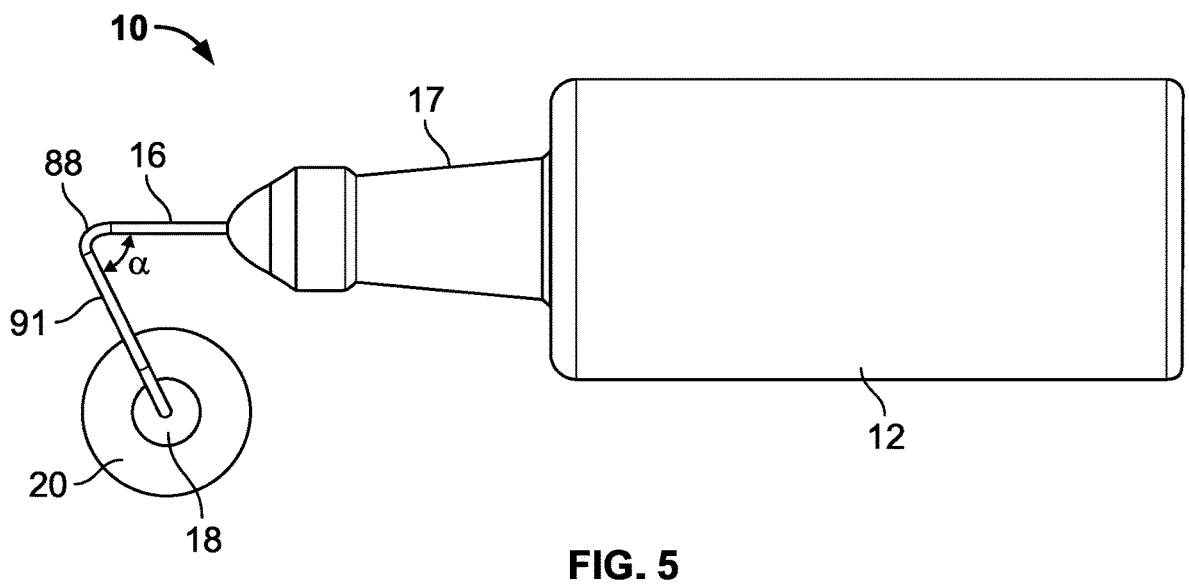
FIG. 5 is a top plan view of the modular fluid path assembly of FIG. 1 with a needle in a bent configuration.
Figure 6:
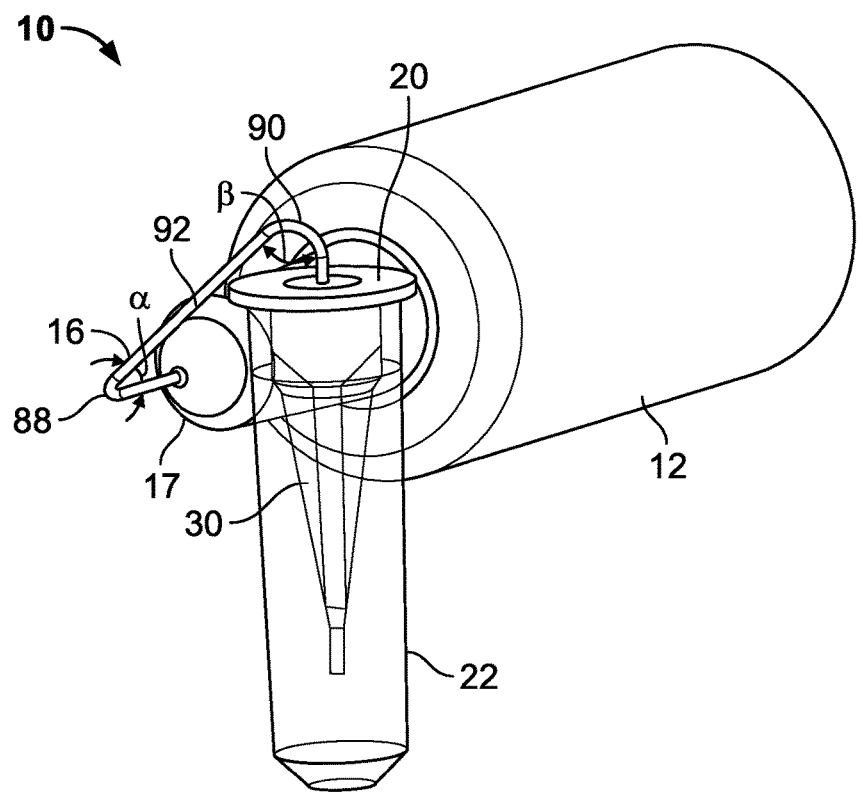
FIG. 6 is a perspective view of the modular fluid path assembly of FIG. 5.

In one embodiment, the syringe 10 can be prepared for assembly into a drug delivery device. As shown in FIGS. 5 and 6, to fit the syringe 10 in the device, the needle 16 can be shaped into a bent configuration including a first bend 88 adjacent to the needle hub 17 and a second bend 90 adjacent to the septum 18. So configured, a portion 91 of the needle 16 extending between the hub 17 and the second bend 90 provides a conduit for the fluid path. Further, the second bend 90 provides a coupling portion for the fluid path, described in more detail below.

In the illustrated form, the first bend 88 is a slightly acute or generally 90 degree bend α, for example between approximately 90 degrees and approximately 70 degrees, so that an intermediate portion 92 of the needle 16 extends away from the longitudinal axis L of the barrel 12. So configured, the bent configuration can position the assembly of the septum 18, cannula 20, and needle shield 22 in an offset position with respect to the barrel 12. As shown, the second bend 90 can have an acute bend β, such that when the assembly is oriented generally vertically with respect to a horizontal plane extending parallel to the longitudinal axis L of the barrel 12, the intermediate portion 92 of the needle 16 extends upwardly at an angle δ with respect to the horizontal plane to the second bend 90. Angle δ can be between about 30 degrees and about 60 degrees, and more specifically about 45 degrees. Additionally, as shown in FIG. 6, the intermediate portion 92 and the forward portion 30 reside in a common vertical plane that intersects the longitudinal axis L and the portion the needle 16 adjacent to the barrel 12.

Bending the needle 16 can be performed by any suitable mechanism and method. In one approach, the cover 78 of the carrier 66 is removed. As shown in FIG. 3, the base portion 76 can include hinge and pivot mechanisms 94 aligned with portions of the needle 16 intended to be bent. Accordingly, when installation of the syringe 10 into a suitable device is desired, a user can remove the cover 78 and manipulate the base portion 76 to create the first and second bends 88, 90 in the needle 16 while the base portion 76 holds the components of the syringe 10 in position relative to one another. The base portion 76 can include stops or guides 96 so that the manipulation of the base portion 76 creates the first and second bends 88, 90 in desired angles and directions. In another approach, the syringe 10 may be removed from the carrier 66 and the first and second bends 88, 90 performed with suitable fixtures or devices. In order to maintain the sterility and CCI of the syringe 10 during the bending process, care can be taken to avoid putting excessive loads on the needle hub 17 and displacing the needle 16, septum 18, or cannula 20 within the needle shield 22.

Figure 7:
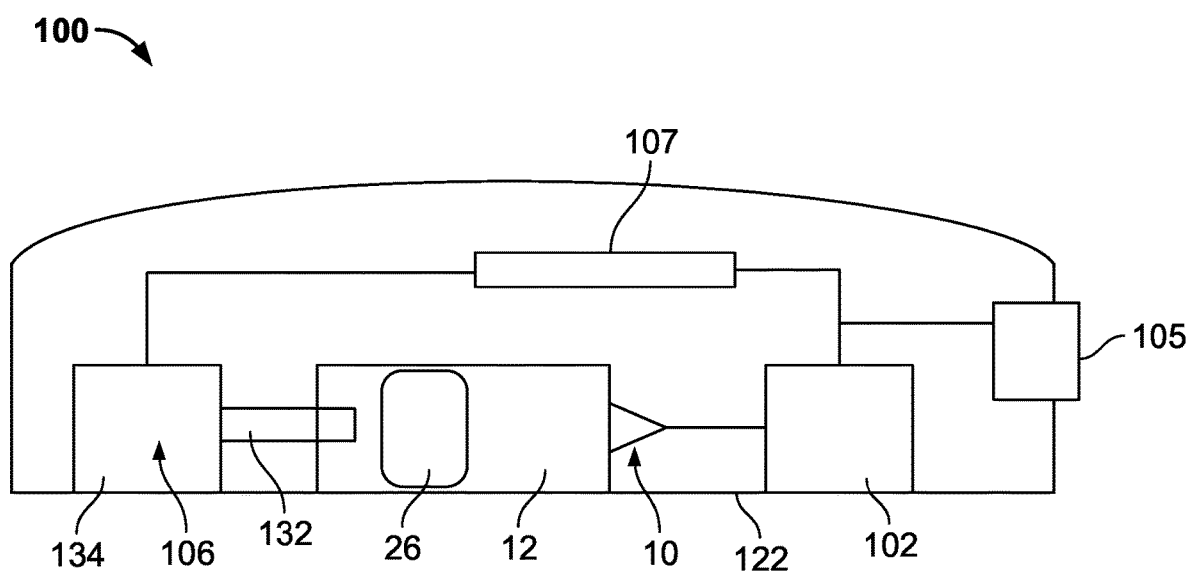
FIG. 7 is a side diagrammatic view of one embodiment of a drug delivery device.
Figure 8:
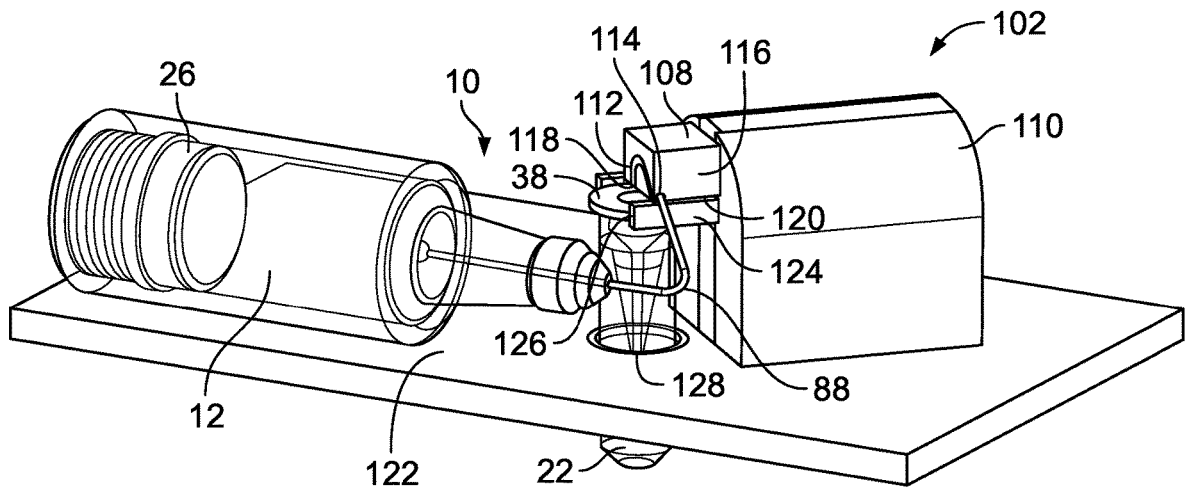
FIG. 8 is a sectional perspective view of one embodiment of a needle insertion mechanism coupled to the modular fluid path assembly of FIG. 5.
Figure 9:
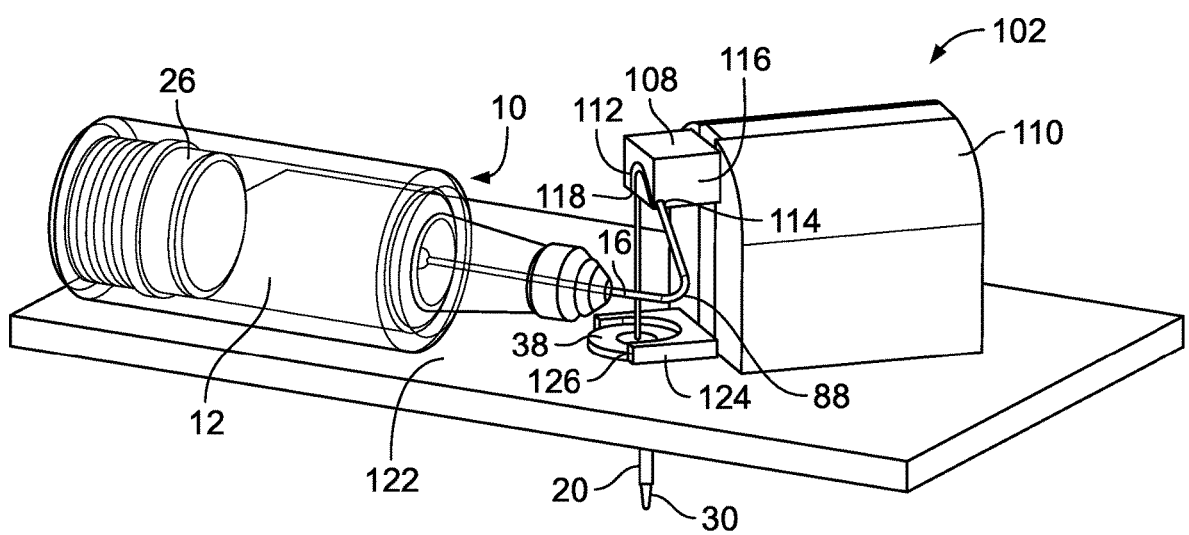
FIG. 9 is a sectional perspective view of the needle insertion mechanism coupled of FIG. 8.

As shown in FIGS. 7-9, the syringe 10 can be installed within an on-body injector drug delivery device 100 having a needle and cannula insertion mechanism (NIM) 102 and a plunger drive mechanism 106. The plunger drive mechanism 106 includes a plunger rod 132 and a drive 134 operably coupled to the plunger rod 132. The drive 134 may be in the form of a spring, pneumatic, hydraulic, or motor driven assembly. The components of the device 100 may be operated by a controller 107, for example, in response to user actuation of an actuator 105. The controller 107 can include a processor and a memory storing logic that is executable by the processor. More specifically, the memory may include one or more tangible non-transitory readable memories having logic (e.g., executable instructions) stored thereon, which instructions when executed by the processor may cause the at least one processor to carry out the actions that the controller is adapted to perform. Additionally, the controller 107 may include other circuitry for carrying out certain actions in accordance with the principles of the present disclosure.

In the form illustrated in FIGS. 8 and 9, the NIM 102 can be a scotch yoke mechanism that includes a needle sliding block 108 and a cannula sliding member 124 projecting forwardly from a housing 110 of the NIM 102. The needle sliding block 108 and cannula sliding member 124 are operably coupled to a crank and drive (not shown) of the NIM 102, as commonly configured, so that rotation of the crank drives linear movement of the block 108 and member 124. The drive can be a spring, pneumatics, hydraulics, a motor, and/or a mechanical linkage.

The needle sliding block 108 includes a slot 112 shaped to receive the second bend 90 of the needle 16 therein during assembly of the pre-sterilized and pre-filled syringe 10. The slot 112 can have a first opening 114 in a side 116 of the block 108 and a second opening 118 in a bottom 120 of the block 108 so that the needle 16 can extend into the block 108 from the side 116 and project out of the block 108 downwardly so that the needle tip 54 projects downwardly below the block 108 toward a bottom wall 122 of the device 100.

The cannula sliding member 124 couples to the cannula 20 to drive the cannula 20 downwardly into a patient. The sliding member 124 includes an inwardly opening groove 126 configured to receive the flange 38 of the cannula 20. The flange 38 can be generally rigid so that movement of the sliding member 124 drives movement of the cannula 20. Further, the sliding member 124 is adapted to hold the cannula 20 in place when a user removes the needle shield 22.

The bottom wall 122 includes a through opening 128 disposed adjacent to the NIM 102 and aligned with the needle shield 22 of the syringe 10 when the syringe 10 is installed in the device 100. As shown, the needle shield 22 preferably projects through the opening 128 to a position where the needle shield 22 can be easily grasped by a user and removed prior to use.

In use, the NIM 102 is configured to insert the needle 16 and cannula 20 through the opening 128 and into subcutaneous tissue of a patient when activated. In one approach, the needle block 108 and the cannula member 124 can have separate couplings to the NIM 102. In other approaches, the NIM 102 may drive both the block 108 and member 124 or can drive the block 108 with the block 108 driving movement of the member 124.

As shown in FIG. 9, the cannula 20 is held in an inserted state during operation of the device 100. By one approach, the cannula member 124 may hold the cannula 20 in place against the housing bottom wall 122 to form a water tight seal against fluid ingress into the device 100. For example, the cannula 20, cannula member 124, and/or the bottom wall 122 can include elastic, adhesive, or force concentrating features to form the seal. In an alternative approach, the cannula member 124 may advance the cannula 20 into a locking mechanism in or on the bottom wall 122. Further, cannula member 124 may be deflected away from the flange 38 during activation so that the flange 38 can fully engage the bottom wall 122 and any sealing features and/or locking mechanisms thereon.

The NIM 102 inserts the needle 16 to the designed depth in subcutaneous tissue and then retracts the needle 16 with the cannula 20 held in the inserted state so that the tip 54 of the needle 16 is disposed within a sharps protected location 130 of the cannula 20 and septum 18. The sharps protected location 130 can preferably be within the open rear portion 63 of the septum bore 40 to maintain the one-way valve functionality of the septum 18 while keeping the needle tip 54 a sufficient distance within the septum 18 for a fluid tight seal. By one approach, the tip 54 of the needle 16 can be steeply beveled, such as approximately 23 degrees, and the needle 16 can be a 27-31 gauge needle, which can combine to minimize the overall height of the assembly while still being comfortable for the patient. Moreover, a needle 16 having a gauge in the range of 27-31 is sufficiently flexible to be rotated and bent, such as due to movement by the block 108 and edges of the first opening 114 acting on the needle 16, to maintain a satisfactory hollow interior for drug delivery and resist crimping or fracturing. Further, due to the flexibility of the needle 16, the needle 16 does not rotate inside of the hub 17 of the barrel 12, such that the seal between the needle 16 and barrel 12 is not compromised by movement driven by the NIM 102.

After the NIM 102, inserts the needle 16 and cannula 20 and retracts the needle 16, the device 100 can then operate the plunger drive mechanism 106. Upon activation, the drive 134 of the plunger drive mechanism moves the plunger rod 132 longitudinally through the barrel 12 until the plunger rod 132 engages and pushes the stopper 26 through the barrel 12 to dispense the medicament 24.

Figure 10:
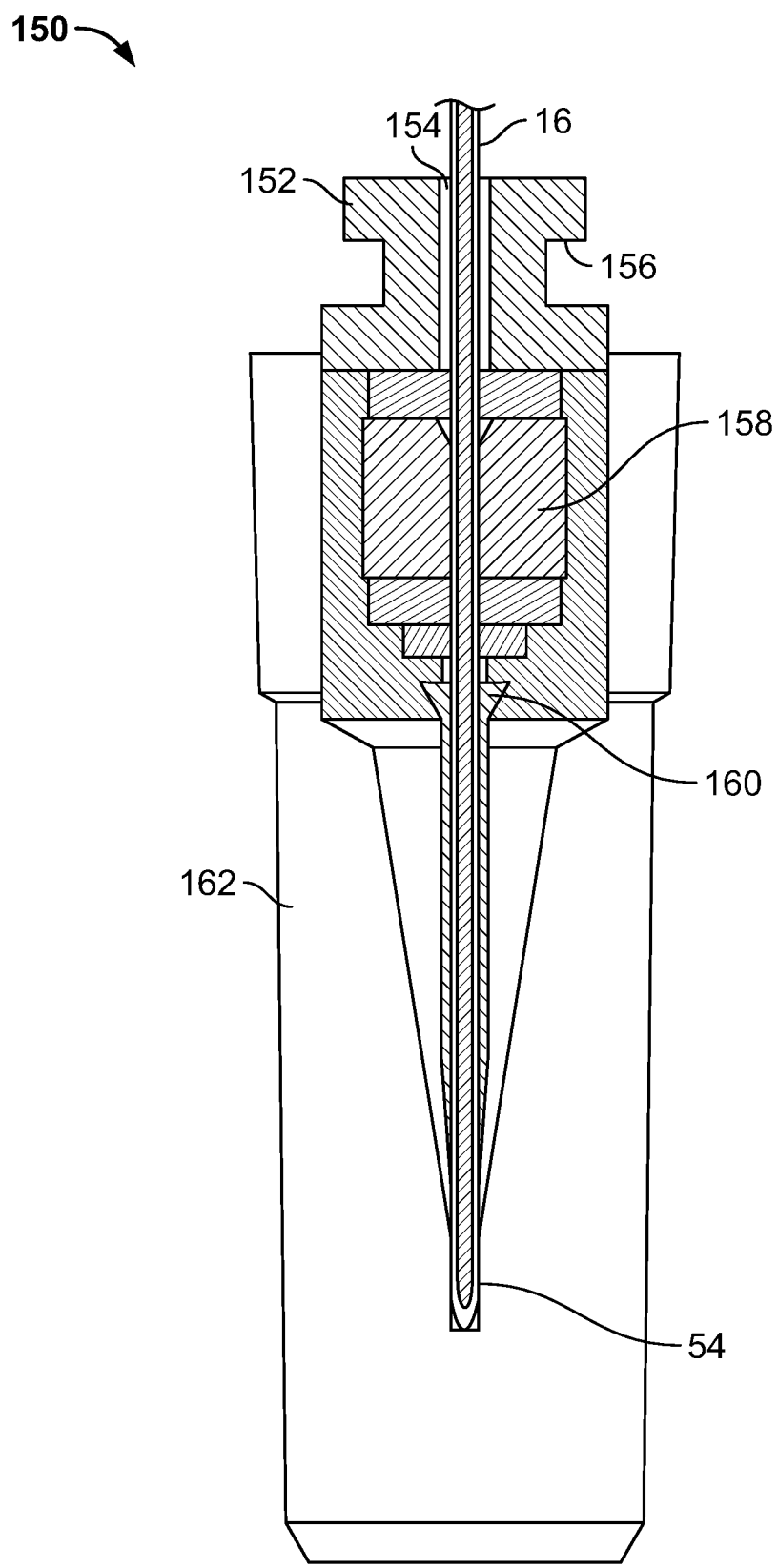
FIG. 10 is a cross-sectional side view of an alternative embodiment of a cannula and septum assembly for the modular fluid path assembly of FIG. 1.
Figure 11:
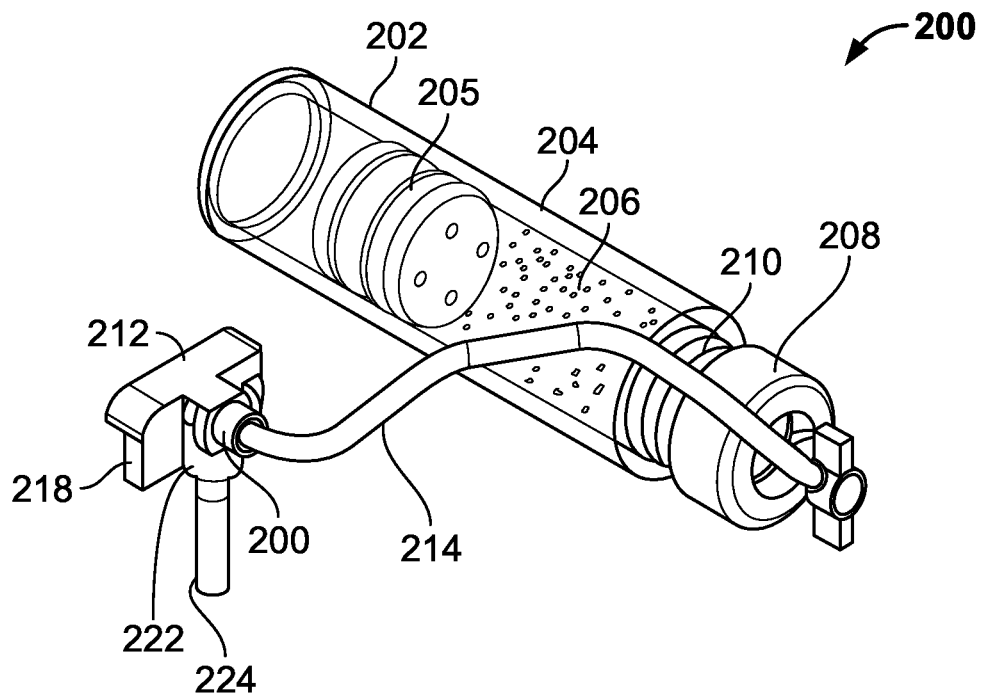
FIG. 11 is a perspective view of another embodiment of a modular fluid path assembly for drug delivery devices.
Figure 12:
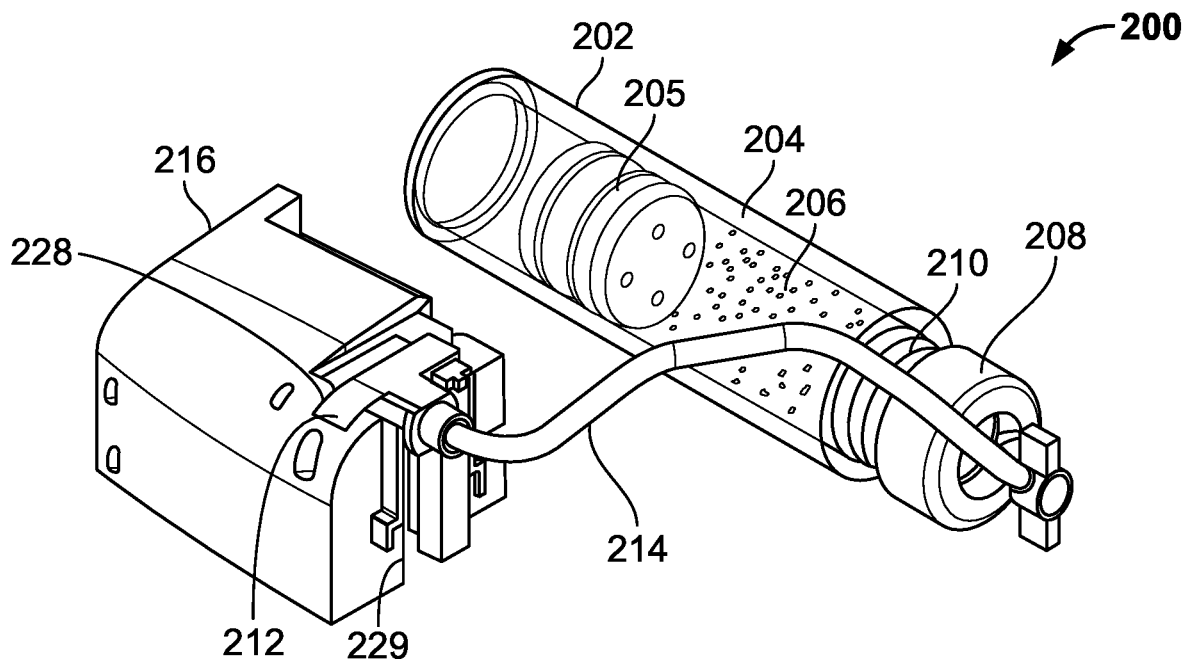
FIG. 12 is a perspective view of the modular fluid path assembly of FIG. 11 coupled to one embodiment of a needle insertion mechanism.

An alternative embodiment for a cannula assembly 150 is shown in FIG. 10. Instead of an outwardly projecting flange 38 as with the above embodiment, this assembly 150 includes a member 152 having a cylindrical configuration with a central bore 154 to receive the needle 16 therethrough and an outwardly facing annular channel or eyelets 156. The member 152 is disposed rearwardly of a septum 158 and cannula 160. A needle shield 162 receives the assembly 150 and can be configured similar to the needle shield 22 described above. The member 152 can be mounted to the needle 16 in a similar fashion as described above with respect to the septum 18, and can form a portion of the septum 158 or be secured to the septum 158 and/or cannula 160.

In this embodiment, the cannula member 124 can include rods or a flange configured to engage the channel 156 with the operation being similar to that described above. In this embodiment, however, the rods would not need to be deflected to seal the cannula 160 to the bottom wall 122 and may instead by used as a locking mechanism for a water tight seal.

Another modular fluid path assembly 200 is described with reference to FIGS. 11-26 that includes a primary container 202 having a tubular body 204, a stopper 205 disposed within the body 204 of the primary container 202, a medicament 206 disposed within the primary container 202 forward of the stopper 205, an end cap 208 mounted on an outlet 210 of the primary container 202, a needle and cannula insertion hub 212 configured to couple to a NIM, and a conduit 214 extending between the end cap 208 and needle and cannula insertion hub 212. The conduit 214 can be generally rigid, flexible, and combinations thereof. After assembly, sterilization, and filling, the modular fluid path assembly 200, between the stopper 205 and an end of a needle 233 within the hub 212, described below, has a CCI seal.

This embodiment allows the primary container 202 and components of the fluid path to be separated from a cannula and needle insertion mechanism (NIM) 216 discussed in more detail below. As such, the modular fluid path assembly 200 has a smaller footprint without the NIM 216, enables more assemblies to fit within sterilization and fill lines, similar to that discussed above with respect to FIGS. 1-4.

Details of the needle and cannula insertion hub 212 are shown in FIGS. 11-16. The hub 212 includes a yoke body 218 having an outwardly extending port 220 connected to the conduit 214, a cannula carrier 222, and a needle shield 224. The yoke body 218 is configured to snap fit to the NIM 216. For this functionality, the yoke body 218 includes lateral wall portions 226 (see, e.g., FIGS. 13 and 14) that fit within an aperture 228 (see, e.g., FIGS. 12 and 14) in the NIM 216 and a rearwardly opening channel 230 (see, e.g., FIG. 13) defined by a top wall 232 and bottom wall 234. The NIM 216 further includes a slot opening 229 extending along a height of the aperture 228 to allow components of the insertion hub 212 to extend forwardly of the NIM 216, such as the port 220, cannula carrier 222, and so forth. The generally T-shaped configuration of the yoke body 218 cooperate with the aperture 228 and slot opening 229 with a tongue-and-groove functionality to couple the components together. As shown in FIGS. 19-23, the hub 212 further includes a needle 233 mounted to the yoke body 218 and fluidly coupled to the port 220 and a cannula 235 mounted to the cannula carrier 222.

Figure 13:
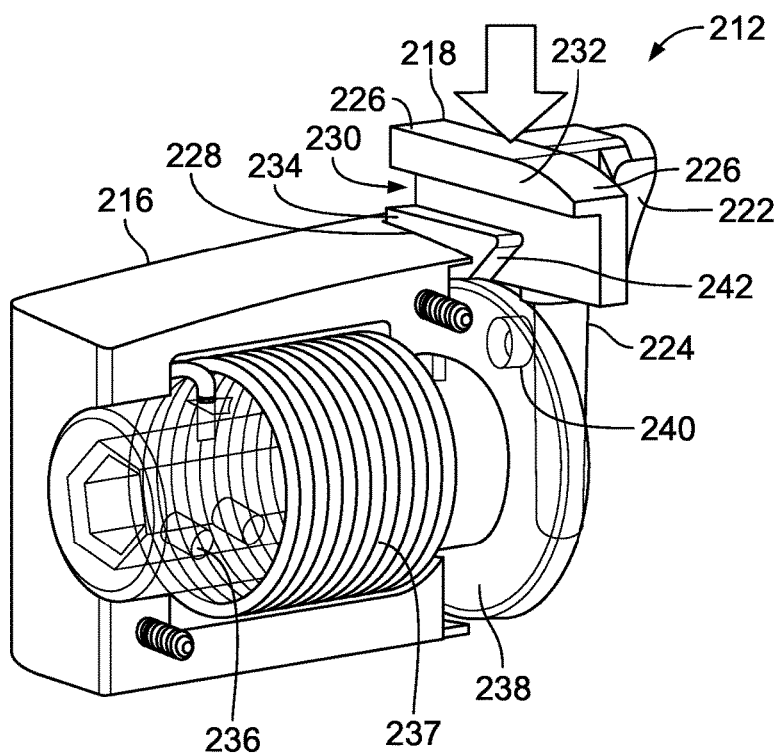
FIG. 13 is a sectional perspective view of an insertion hub of the modular fluid path assembly being coupled to the needle insertion mechanism of FIG. 12.
Figure 14:
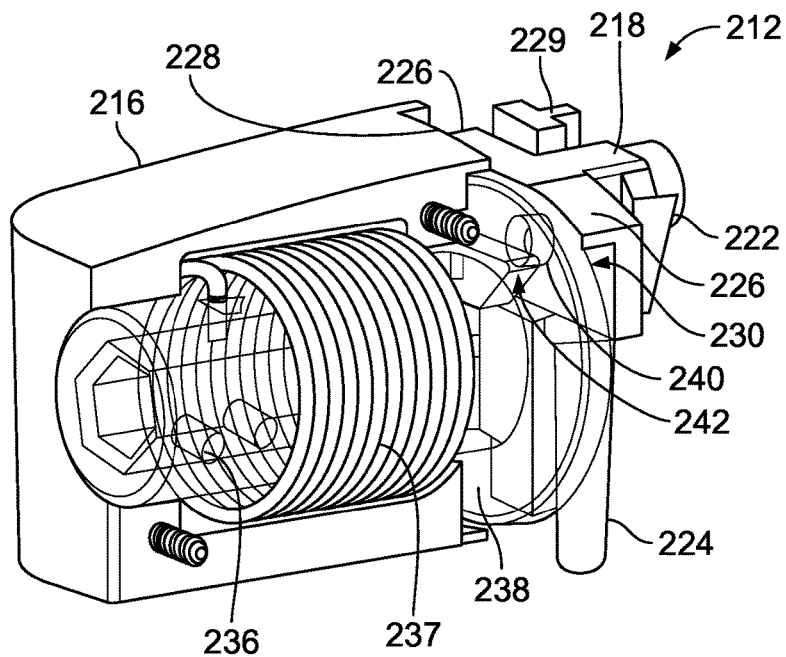
FIG. 14 is a sectional perspective view of an insertion hub of the modular fluid path assembly being coupled to the needle insertion mechanism of FIG. 12.

The NIM 216 is a scotch yoke rotary to linear conversion device that includes a rolling scotch member 236 driving movement of the sliding yoke body 218 using a spring 237. Pneumatics, hydraulics, motors, and mechanical linkages can alternatively be utilized. The scotch member 236 includes a disc-shaped crank 238 having a drive pin 240 projecting outwardly from a spaced radial position on the crank 238. As shown in FIG. 13, the bottom wall 234 defining the channel 230 of the yoke body 218 includes a downwardly facing angled surface 242 that engages the drive pin 240 as the yoke body 218 is slid into the aperture 228. The angled surface 242 radially displaces the drive pin 240 in opposition to the spring 237 until the drive pin 240 aligns with the channel 230 and the spring 237 drives the drive pin 240 into the channel 230. The NIM 216 is held in this charged state until injection is desired.

Figure 15:
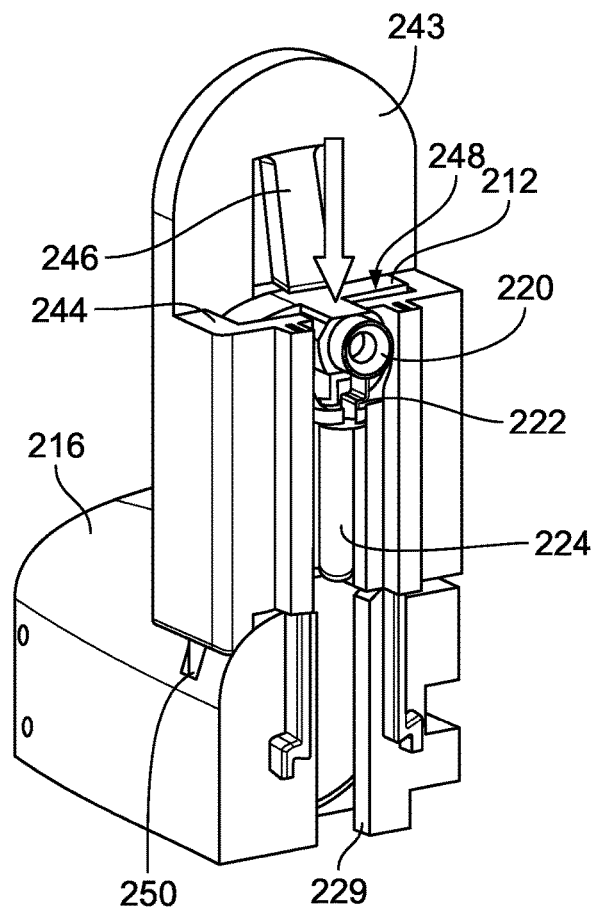
FIG. 15 is a perspective view of one embodiment of an assembly aid for the insertion hub of the modular fluid path assembly to be coupled to the needle insertion mechanism of FIG. 12.

If desired, the needle and cannula insertion hub 212 can be inserted into an assembly aid 243 that both protects the components of the insertion hub 212 and also facilitates assembly of the insertion hub 212 into the aperture 228 of the NIM 216. As shown in FIG. 15, the assembly aid 243 includes an interior slot 244 sized to receive the insertion hub 212. A resilient retention catch 246 projects over an open top 248 of the slot 244, such that the catch 246 is deflected when the insertion hub 212 is inserted through the open top 248. The catch 246 then resiliently returns to position over the open top 248 to prevent the insertion hub 212 from sliding out of the slot 244.

The assembly aid 243 can then mount to the NIM 216, such as by cooperating tabs and openings 250, so that the slot 244 of the assembly aid 243 aligns with the aperture 228 of the NIM 216. Then a user, or an automated process, need only slide the insertion hub 212 downward into the aperture 228 of the NIM 216 until the drive pin 240 is deflected and pivoted into the channel 230 to hold the insertion hub 212 in a storage position.

Figure 16:
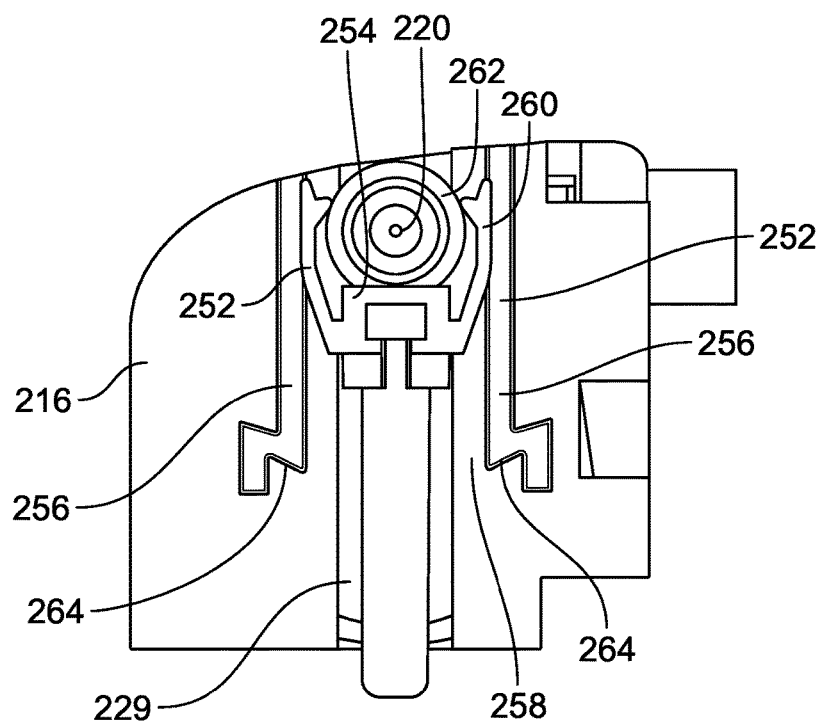
FIG. 16 is a sectional front view of the insertion hub of the modular fluid path assembly mounted within the needle insertion mechanism of FIG. 12.

As shown in FIG. 16, the cannula carrier 222 includes arms 252 that project upwardly at an angle from a main portion 254 of the carrier 222. With the insertion hub 212 mounted to the NIM 216, the arms 252 are resiliently deflected inwardly by walls 256 running along edge portions 258 of the slot opening 229. In the illustrated form, the arms 252 includes retention catches 260 that project inwardly to engage upper surfaces 262 of the yoke body 218 when the arms 252 are in the deflected position to thereby operably couple the carrier 222 to the yoke body 218. Further, the walls 256 define locking tabs 264 at ends thereof so that as the NIM 216 drives the yoke body 218 and the carrier 222 downwardly, the arms 252 resiliently flex outwardly into the locking tabs 264. As such, when the yoke body 218 is driven back upward by the NIM 216, the locking tabs 264 prevent the carrier 222 moving upward.

Figure 17:
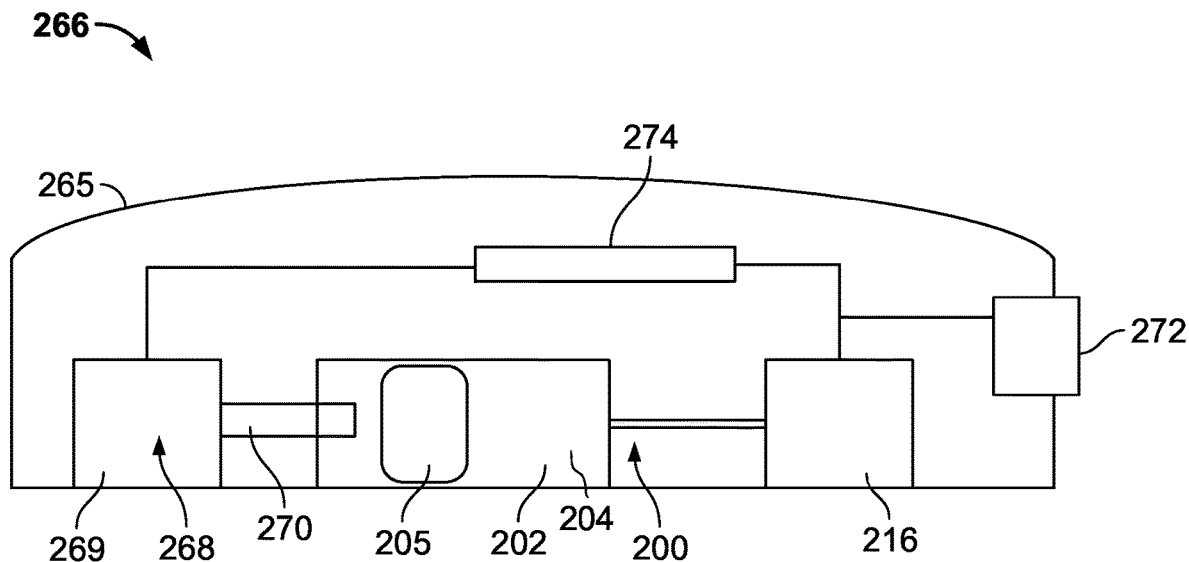
FIG. 17 is a side diagrammatic view of one embodiment of a drug delivery device.
Figure 18:
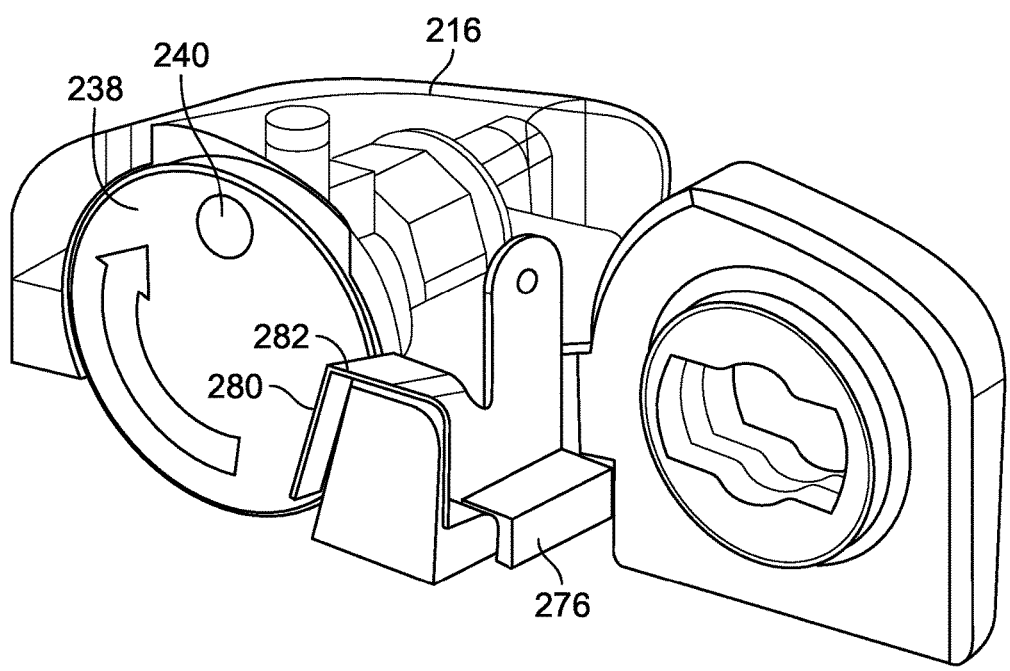
FIG. 18 is a sectional view of one embodiment of a needle insertion mechanism.
Figure 19:
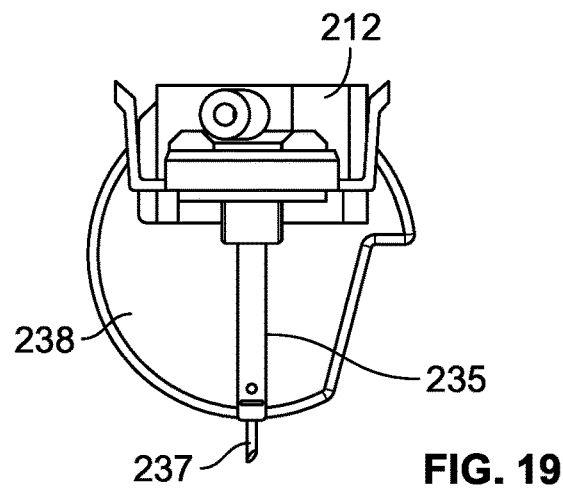
FIGS. 19 to 23 are front elevational views of one embodiment of a needle and cannula insertion and retraction process.
Figure 20:
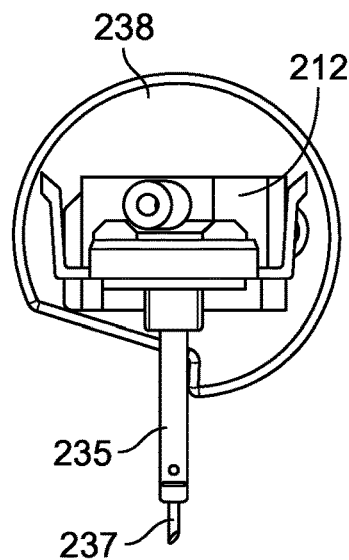
Figure 21:
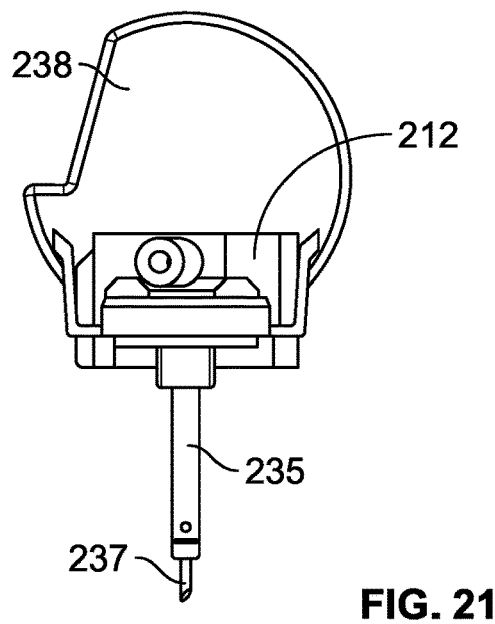

With this configuration, the modular fluid path assembly 200 can be easily installed within a housing 265 of an on-body injector drug delivery device (OBI) 266 having the NIM 216 disposed therein as illustrated in FIG. 17. As with the above device 100, the OBI 266 of this form can include a similarly configured plunger drive mechanism 268, described in detail above, that is configured so that a drive 269 moves a plunger rod 270 to engage the stopper 205 of the assembly 200 when the assembly 200 is installed in the OBI 266. The OBI 266 may further include a controller 274 configured to control operation of the components of the OBI 266. The controller 274 can include a processor and a memory storing logic that is executable by the processor. More specifically, the memory may include one or more tangible non-transitory readable memories having logic (e.g., executable instructions) stored thereon, which instructions when executed by the processor may cause the at least one processor to carry out the actions that the controller is adapted to perform. Additionally, the controller 274 may include other circuitry for carrying out certain actions in accordance with the principles of the present disclosure.

Additional details of the insertion process are shown in FIGS. 18-23. When insertion is desired, such as in response to user actuation of an actuator 272 of the OBI 266, the controller 274 of the OBI 266 can send a signal to the NIM 216 to operate a trigger 276 and release the spring 237. In the illustrated form, the crank 238 includes a cut-out portion 280 having a stop surface 282 configured to engage the trigger 276 to hold the spring 237 in a charged state. To release the spring 237, the trigger 276 is shifted out of engagement with the crank 238.

Figure 22:
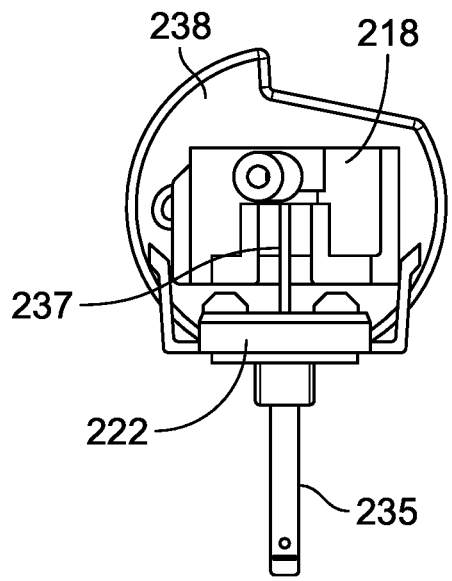
Figure 23:
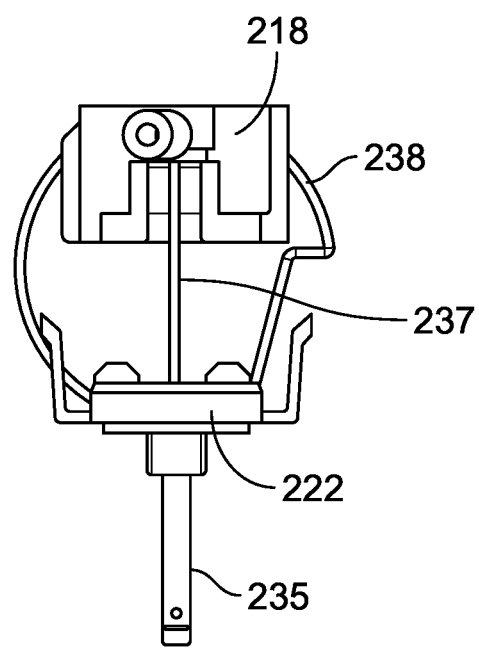

When the spring 237 is released, the spring 237 drives rotation of the scotch member 237. As such, the drive pin 240 rotates 180 degrees while sliding in the channel 230 of the yoke body 218 to drive the yoke body 218 to a fully inserted position. As shown, in FIGS. 19-21, this inserts both the needle 233 and cannula 235 into a patient. Additionally, in this position, the arms 252 of the carrier 222 lock into deflect into the locking tabs 264 to hold the cannula 235 in an inserted position. As shown in FIGS. 22 and 23, the spring 237 continues to drive rotation of the drive pin 237 such that the drive pin 237 completes a full 360 degree rotation. As the drive pin 237 starts rotating back upward, the drive pin 237 slides the yoke body 218 and the needle 233 upward.

To stop the injection operation, the NIM 218 can include a ball bearing 284 disposed in a track 286 a first portion 288 defined by the housing 265 and a second portion 290 defined by the scotch member 236, where the first and second portions 288, 290 are rotatable with respect to one another. The housing portion 288 of the track 286 includes first and second ends 292, 294 and the scotch member portion 290 of the track 286 includes first and second ends 296, 298.

Figure 24:
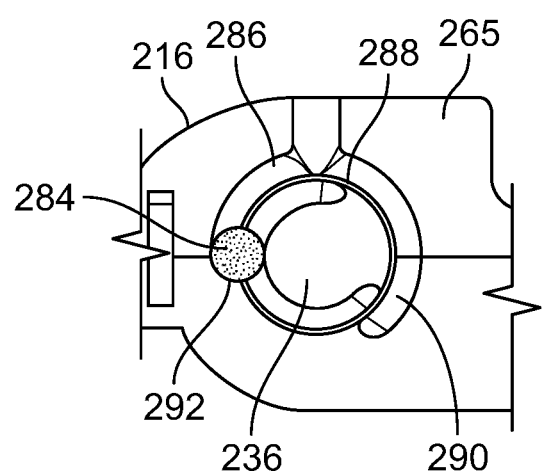
FIGS. 24 to 26 are front elevational views of one embodiment of a ball bearing stop for a needle insertion mechanism.
Figure 25:
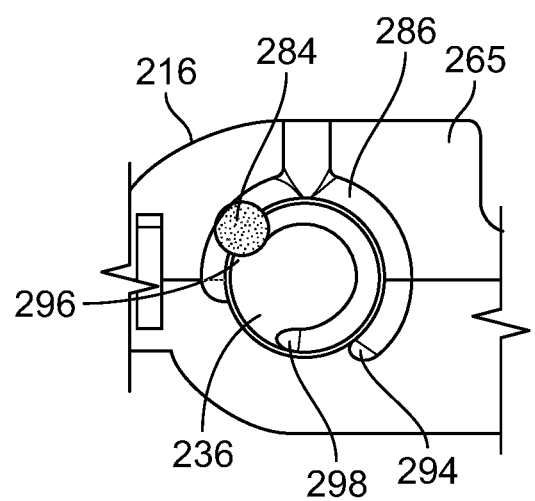
Figure 26:
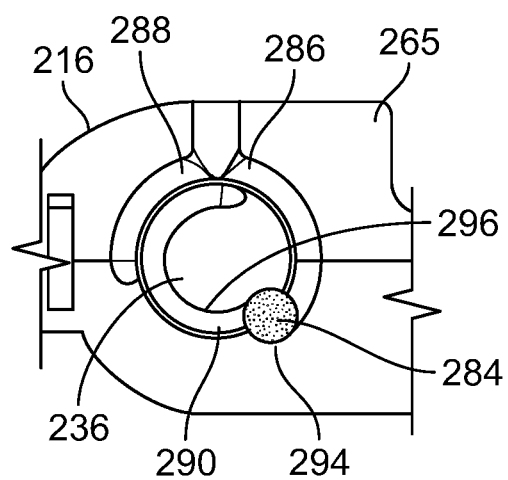
Figure 27:
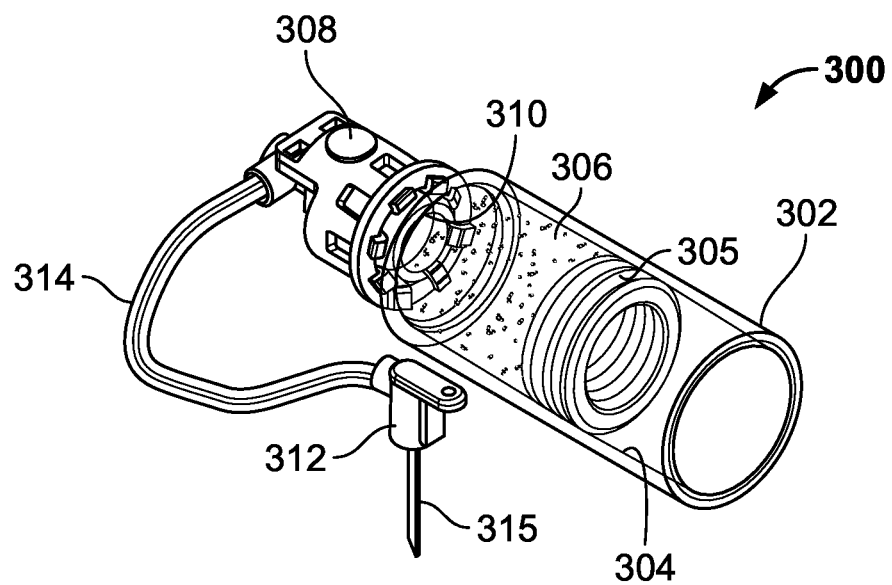
FIG. 27 is a perspective view of another embodiment of a modular fluid path assembly.

As shown in FIGS. 24-26, the ball bearing 284 starts at the first end 292 of the housing portion 288 of the track 286. Thereafter, the spring 237 drives rotation of the scotch member 236 so that the housing and scotch member portions 288, 290 of the track 286 align. Thereafter, the first end 296 of the scotch member portion 290 of the track 286 moves the ball bearing 284 along the housing portion 288 of the track 286 until the ball bearing 284 is trapped between the first end 296 of the scotch member portion 290 of the track 286 and the second end 294 of the housing portion 288 of the track 286, effectively stopping rotation of the scotch member 236 and therefore the insertion operation. The track 286 can be sized to allow any desired amount of rotation, such as a full 360 degree rotation as described above.

Another modular fluid path assembly 300 is described with reference to FIGS. 27-33 that includes a primary container 302 having a tubular body 304, a stopper 305 disposed within the body 304 of the primary container 302, a medicament 306 disposed within the primary container 302 forward of the stopper 303, an end cap 308 mounted on an outlet 310 of the primary container 302, a needle insertion hub 312 configured to couple to a NIM, and a conduit 314 extending between the end cap 308 and needle insertion hub 312. The conduit 314 can be generally rigid, flexible, and combinations thereof. As discussed in more detail below, the fluid path assembly 300 can further include a needle shield 313 and a needle 315 mounted to the needle insertion hub 312 to be fluidly coupled to the conduit 314. After assembly, sterilization, and filling, the modular fluid path assembly 300, between the stopper 303 and an end of a needle 315 embedded within the needle shield 313 has a CCI seal.

This embodiment allows the primary container 302 and components of the fluid path to be separated from a needle insertion mechanism (NIM) 316 discussed in more detail below. As such, the modular fluid path assembly 300 has a smaller footprint without the NIM 316, enabling more assemblies to fit within sterilization and fill lines, as discussed above.

The NIM 316 is a scotch yoke rotary to linear conversion device that includes a rolling scotch member 318 driving movement of a sliding yoke member 320 using a spring 322. Pneumatics, hydraulics, motors, and mechanical linkages can alternatively be utilized. The scotch member 318 includes a disc-shaped crank 324 having a drive pin (not shown) projecting outwardly from a spaced radial position on the crank 324. The yoke member 320 includes a horizontal channel 326 in which the pin slides to drive the yoke member 320 upward and downwardly through a full revolution. The NIM 316 is held with the spring 322 in a charged state until needle insertion is desired.

Figure 29:
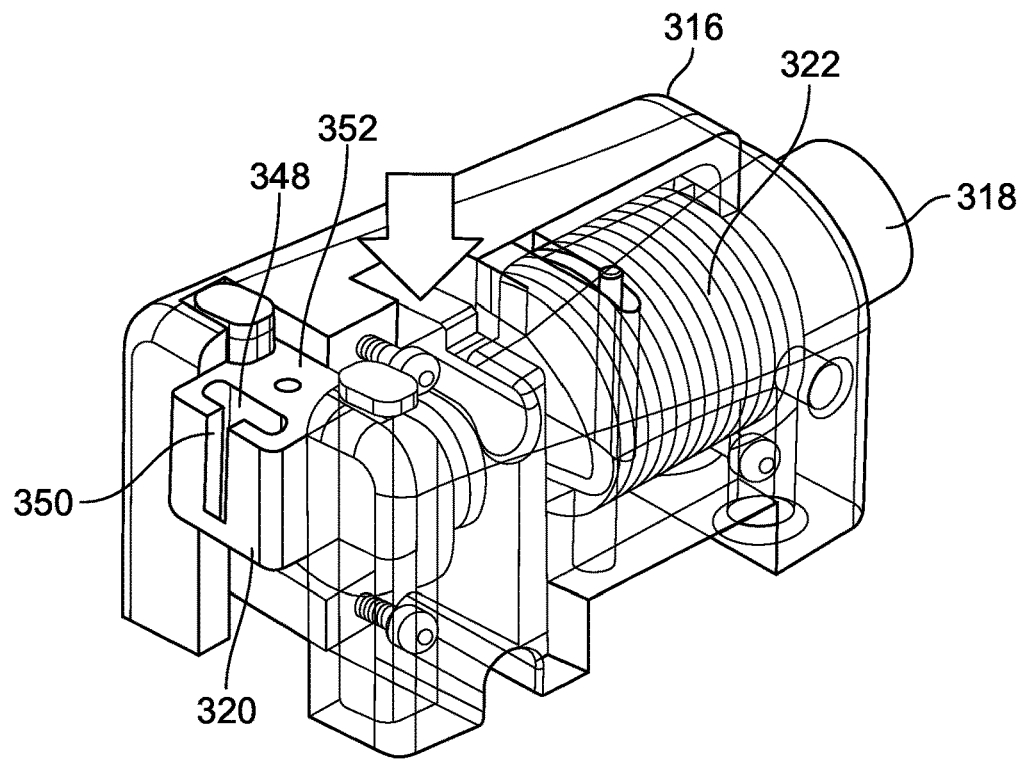
FIG. 29 is a perspective view of one embodiment of a needle insertion mechanism showing a first operation trigger.
Figure 30:
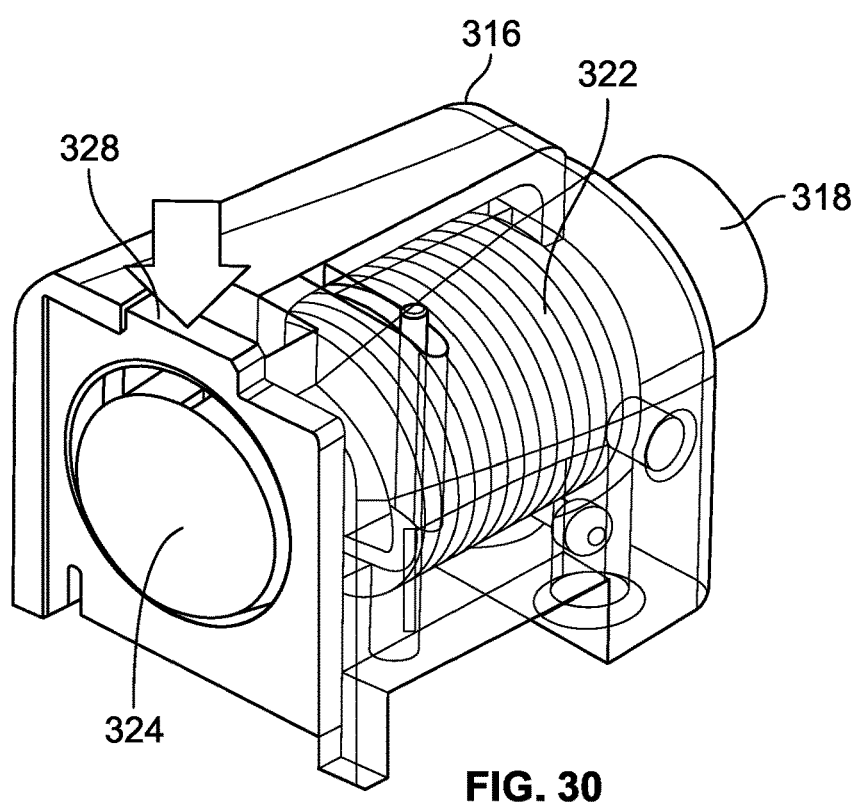
FIG. 30 is a cross-sectional view of the needle insertion mechanism of FIG. 29.
Figure 31:
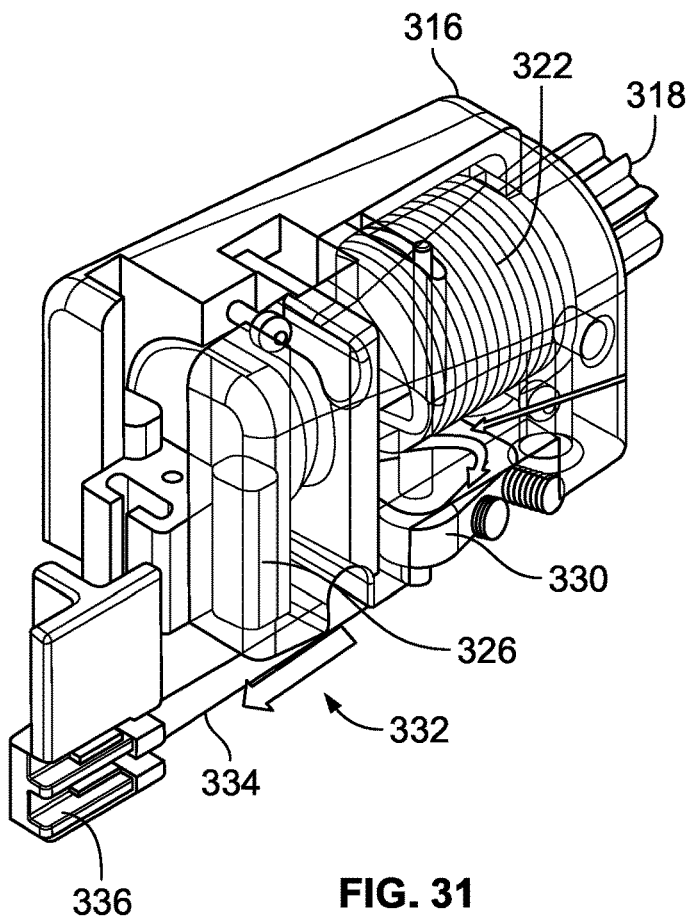
FIG. 31 is a top perspective view of the needle insertion mechanism of FIG. 29 showing a second operation trigger.
Figure 32:
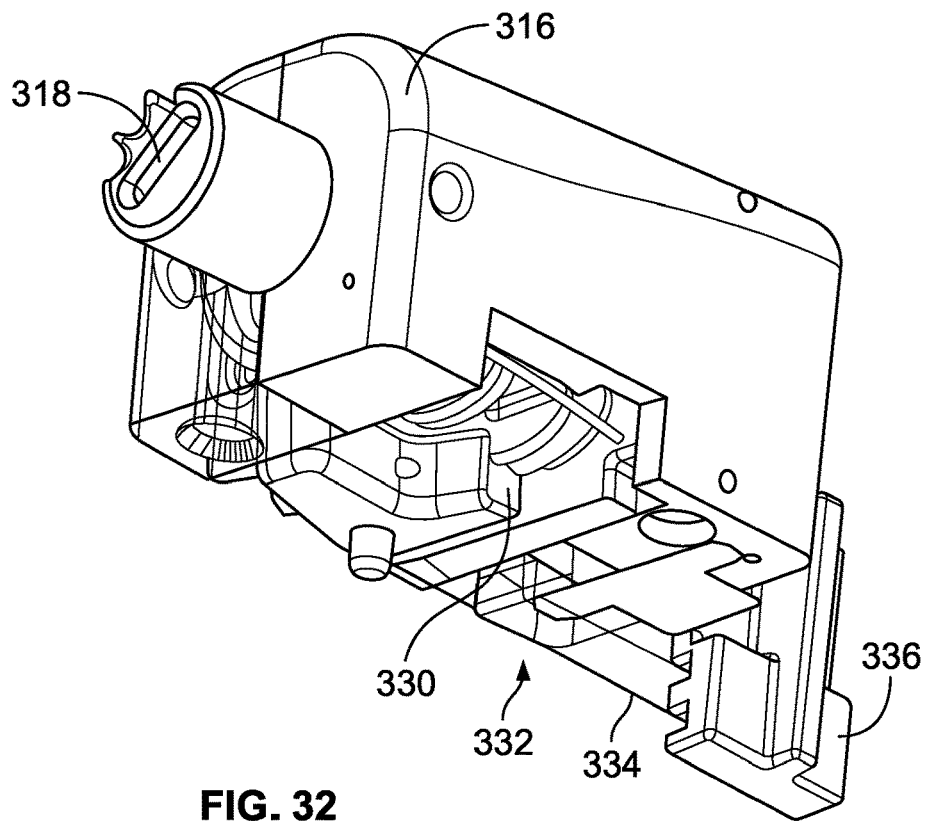
FIG. 32 is a bottom perspective view of the needle insertion mechanism of FIG. 31.

With the needle 315 being utilizes to inject the medicament 306 subcutaneously in a patient, the NIM 316 can have a two stage operation with a first stage inserting the needle 315 to a desired subcutaneous depth and a delayed second stage to retract the needle 315 after a predetermined amount of medicament 306 has been dispensed. In a first approach, as shown in FIGS. 29 and 30, the NIM 316 can include a first trigger 328 that shifts to release the scotch member 318 until it abuts a stop 330 generally halfway through a revolution with the needle 315 fully inserted. Then, as shown in FIGS. 31 and 32, the NIM 316 can include a second trigger 332 that includes muscle wire 334 coupled to the stop 330 and a base 336, where the muscle wire 334 pivots the stop 330 out of engagement with the scotch member 318 so that scotch member 318 can complete a full revolution to retract the needle 315. The delay between completing the full insertion of the needle and operating the second trigger 332 can correspond to the time needed to dispense a predetermined amount of medicament 306. Of course, other configurations can be utilized, such as a channel with a dwell and other stop and release mechanisms.

Figure 28:
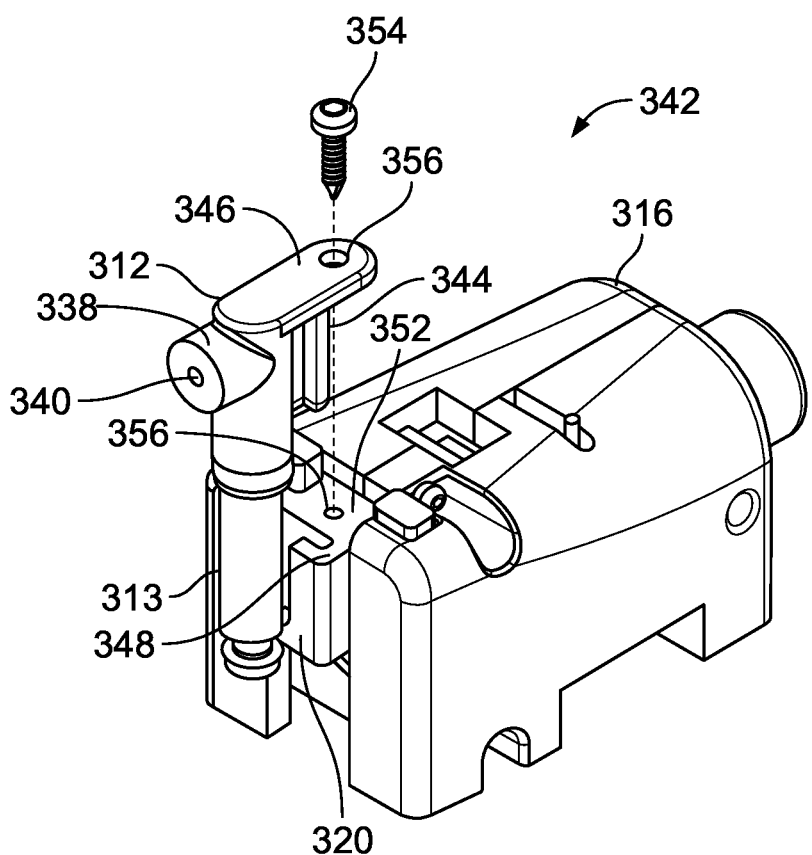
FIG. 28 is a perspective view of a needle hub of the modular fluid path assembly of FIG. 27 being mounted to a needle insertion mechanism.

Details of the needle insertion hub 312 and the connection to the NIM 316 are shown in FIGS. 28 and 29. The hub 312 includes a body 338 with a forwardly extending port 340 fluidly coupled to the conduit 314 and a rearwardly extending coupling portion 342. The coupling portion 342 includes a T-shaped rib 344 and a top tab 346. The yoke member 320 of the NIM 316 includes a corresponding aperture 348 with a slot opening 350 configured to sliding receive the T-shaped rib 344. Further, as shown, with the rib 344 inserted into the aperture 348, the top tab 346 projects over a top surface 352 of the yoke member 320. As such, a fastener 354, such as a screw as shown, can secure the needle insertion hub 312 to the yoke member 320. The tab 346 and yoke member 320 may include openings 356 to threadingly receive the fastener 354. Other securing mechanisms can be utilized, such as snap-fit, adhesive, and so forth.

Figure 33:
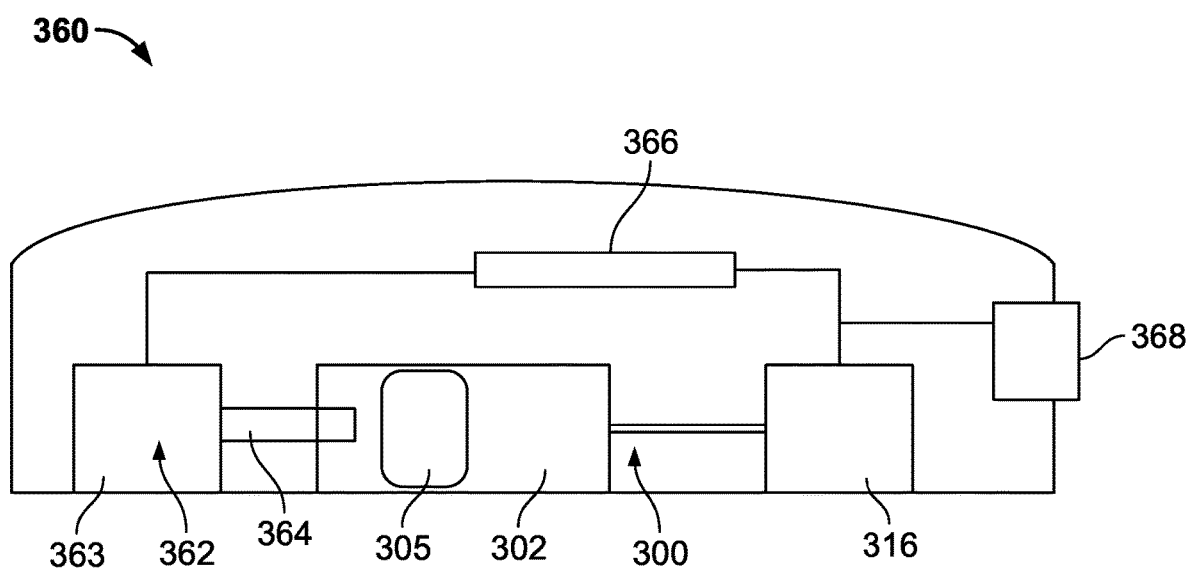
FIG. 33 is a side diagrammatic view of one embodiment of a drug delivery device.

With this configuration, the modular fluid path assembly 300 can be easily installed within a housing 358 of an on-body injector drug delivery device (OBI) 360 having the NIM 316 disposed therein as shown in FIG. 33. As with the above device 100, the OBI 360 of this form can include a similarly configured plunger drive mechanism 362, described in detail above, that includes a drive 363 that is configured to move a plunger rod 364 of the mechanism 362 to engage the stopper 305 of the assembly 300 when the assembly 300 is installed in the OBI 360. The OBI 360 may further include a controller 366 configured to operate the components of the OBI 360. The controller 366 can include a processor and a memory storing logic that is executable by the processor. More specifically, the memory may include one or more tangible non-transitory readable memories having logic (e.g., executable instructions) stored thereon, which instructions when executed by the processor may cause the at least one processor to carry out the actions that the controller is adapted to perform. Additionally, the controller 366 may include other circuitry for carrying out certain actions in accordance with the principles of the present disclosure. When operation of the OBI 360 is desired, such as in response to user actuation of an actuator 368 of the OBI 266, the controller 366 of the OBI 360 can send a activation signal to the NIM 316 to sequentially operate the first and second trigger 328, 332.

The above description describes various assemblies, devices, and methods for use with a drug delivery device. It should be clear that the assemblies, drug delivery devices, or methods can further comprise use of a medicament listed below with the caveat that the following list should neither be considered to be all inclusive nor limiting. The medicament will be contained in a reservoir. In some instances, the reservoir is a primary container that is either filled or pre-filled for treatment with the medicament. The primary container can be a cartridge or a pre-filled syringe.

For example, the drug delivery device or more specifically the reservoir of the device may be filled with colony stimulating factors, such as granulocyte colony-stimulating factor (G-CSF). Such G-CSF agents include, but are not limited to, Neupogen® (filgrastim) and Neulasta® (pegfilgrastim). In various other embodiments, the drug delivery device may be used with various pharmaceutical products, such as an erythropoiesis stimulating agent (ESA), which may be in a liquid or a lyophilized form. An ESA is any molecule that stimulates erythropoiesis, such as Epogen® (epoetin alfa), Aranesp® (darbepoetin alfa), Dynepo® (epoetin delta), Mircera® (methyoxy polyethylene glycol-epoetin beta), Hematide®, MRK-2578, INS-22, Retacrit® (epoetin zeta), Neorecormon® (epoetin beta), Silapo® (epoetin zeta), Binocrit® (epoetin alfa), epoetin alfa Hexal, Abseamed® (epoetin alfa), Ratioepo® (epoetin theta), Eporatio® (epoetin theta), Biopoin® (epoetin theta), epoetin alfa, epoetin beta, epoetin zeta, epoetin theta, and epoetin delta, as well as the molecules or variants or analogs thereof as disclosed in the following patents or patent applications, each of which is herein incorporated by reference in its entirety: U.S. Pat. Nos. 4,703,008; 5,441,868; 5,547,933; 5,618,698; 5,621,080; 5,756,349; 5,767,078; 5,773,569; 5,955,422; 5,986,047; 6,583,272; 7,084,245; and 7,271,689; and PCT Publication Nos. WO 91/05867; WO 95/05465; WO 96/40772; WO 00/24893; WO 01/81405; and WO 2007/136752.

An ESA can be an erythropoiesis stimulating protein. As used herein, "erythropoiesis stimulating protein" means any protein that directly or indirectly causes activation of the erythropoietin receptor, for example, by binding to and causing dimerization of the receptor. Erythropoiesis stimulating proteins include erythropoietin and variants, analogs, or derivatives thereof that bind to and activate erythropoietin receptor; antibodies that bind to erythropoietin receptor and activate the receptor; or peptides that bind to and activate erythropoietin receptor. Erythropoiesis stimulating proteins include, but are not limited to, epoetin alfa, epoetin beta, epoetin delta, epoetin omega, epoetin iota, epoetin zeta, and analogs thereof, pegylated erythropoietin, carbamylated erythropoietin, mimetic peptides (including EMP1/hematide), and mimetic antibodies. Exemplary erythropoiesis stimulating proteins include erythropoietin, darbepoetin, erythropoietin agonist variants, and peptides or antibodies that bind and activate erythropoietin receptor (and include compounds reported in U.S. Publication Nos. 2003/0215444 and 2006/0040858, the disclosures of each of which is incorporated herein by reference in its entirety) as well as erythropoietin molecules or variants or analogs thereof as disclosed in the following patents or patent applications, which are each herein incorporated by reference in its entirety: U.S. Pat. Nos. 4,703,008; 5,441,868; 5,547,933; 5,618,698; 5,621,080; 5,756,349; 5,767,078; 5,773,569; 5,955,422; 5,830,851; 5,856,298; 5,986,047; 6,030,086; 6,310,078; 6,391,633; 6,583,272; 6,586,398; 6,900,292; 6,750,369; 7,030,226; 7,084,245; and 7,217,689; U.S. Publication Nos. 2002/0155998; 2003/0077753; 2003/0082749; 2003/0143202; 2004/0009902; 2004/0071694; 2004/0091961; 2004/0143857; 2004/0157293; 2004/0175379; 2004/0175824; 2004/0229318; 2004/0248815; 2004/0266690; 2005/0019914; 2005/0026834; 2005/0096461; 2005/0107297; 2005/0107591; 2005/0124045; 2005/0124564; 2005/0137329; 2005/0142642; 2005/0143292; 2005/0153879; 2005/0158822; 2005/0158832; 2005/0170457; 2005/0181359; 2005/0181482; 2005/0192211; 2005/0202538; 2005/0227289; 2005/0244409; 2006/0088906; and 2006/0111279; and PCT Publication Nos. WO 91/05867; WO 95/05465; WO 99/66054; WO 00/24893; WO 01/81405; WO 00/61637; WO 01/36489; WO 02/014356; WO 02/19963; WO 02/20034; WO 02/49673; WO 02/085940; WO 03/029291; WO 2003/055526; WO 2003/084477; WO 2003/094858; WO 2004/002417; WO 2004/002424; WO 2004/009627; WO 2004/024761; WO 2004/033651; WO 2004/035603; WO 2004/043382; WO 2004/101600; WO 2004/101606; WO 2004/101611; WO 2004/106373; WO 2004/018667; WO 2005/001025; WO 2005/001136; WO 2005/021579; WO 2005/025606; WO 2005/032460; WO 2005/051327; WO 2005/063808; WO 2005/063809; WO 2005/070451; WO 2005/081687; WO 2005/084711; WO 2005/103076; WO 2005/100403; WO 2005/092369; WO 2006/50959; WO 2006/02646; and WO 2006/29094.

Examples of other pharmaceutical products for use with the device may include, but are not limited to, antibodies such as Vectibix® (panitumumab), Xgeva™ (denosumab) and Prolia™ (denosamab); other biological agents such as Enbrel® (etanercept, TNF-receptor/Fc fusion protein, TNF blocker), Neulasta® (pegfilgrastim, pegylated filgrastim, pegylated G-CSF, pegylated hu-Met-G-CSF), Neupogen® (filgrastim, G-CSF, hu-MetG-CSF), and Nplate® (romiplostim); small molecule drugs such as Sensipar® (cinacalcet). The device may also be used with a therapeutic antibody, a polypeptide, a protein or other chemical, such as an iron, for example, ferumoxytol, iron dextrans, ferric glyconate, and iron sucrose. The pharmaceutical product may be in liquid form, or reconstituted from lyophilized form.

Among particular illustrative proteins are the specific proteins set forth below, including fusions, fragments, analogs, variants or derivatives thereof:

OPGL specific antibodies, peptibodies, and related proteins, and the like (also referred to as RANKL specific antibodies, peptibodies and the like), including fully humanized and human OPGL specific antibodies, particularly fully humanized monoclonal antibodies, including but not limited to the antibodies described in PCT Publication No. WO 03/002713, which is incorporated herein in its entirety as to OPGL specific antibodies and antibody related proteins, particularly those having the sequences set forth therein, particularly, but not limited to, those denoted therein: 9H7; 18G2; 2D8; 2E11; 16E1; and 22B3, including the OPGL specific antibodies having either the light chain of SEQ ID NO:2 as set forth therein in FIG. 2 and/or the heavy chain of SEQ ID NO:4, as set forth therein in FIG. 4, each of which is individually and specifically incorporated by reference herein in its entirety fully as disclosed in the foregoing publication;

Myostatin binding proteins, peptibodies, and related proteins, and the like, including myostatin specific peptibodies, particularly those described in U.S. Publication No. 2004/0181033 and PCT Publication No. WO 2004/058988, which are incorporated by reference herein in their entirety particularly in parts pertinent to myostatin specific peptibodies, including but not limited to peptibodies of the mTN8-19 family, including those of SEQ ID NOS:305-351, including TN8-19-1 through TN8-19-40, TN8-19 con1 and TN8-19 con2; peptibodies of the mL2 family of SEQ ID NOS:357-383; the mL15 family of SEQ ID NOS:384-409; the mL17 family of SEQ ID NOS:410-438; the mL20 family of SEQ ID NOS:439-446; the mL21 family of SEQ ID NOS:447-452; the mL24 family of SEQ ID NOS:453-454; and those of SEQ ID NOS:615-631, each of which is individually and specifically incorporated by reference herein in their entirety fully as disclosed in the foregoing publication;

IL-4 receptor specific antibodies, peptibodies, and related proteins, and the like, particularly those that inhibit activities mediated by binding of IL-4 and/or IL-13 to the receptor, including those described in PCT Publication No. WO 2005/047331 or PCT Application No. PCT/US2004/37242 and in U.S. Publication No. 2005/112694, which are incorporated herein by reference in their entirety particularly in parts pertinent to IL-4 receptor specific antibodies, particularly such antibodies as are described therein, particularly, and without limitation, those designated therein: L1H1; L1H2; L1H3; L1H4; L1H5; L1H6; L1H7; L1H8; L1H9; L1H10; L1H11; L2H1; L2H2; L2H3; L2H4; L2H5; L2H6; L2H7; L2H8; L2H9; L2H10; L2H11; L2H12; L2H13; L2H14; L3H1; L4H1; L5H1; L6H1, each of which is individually and specifically incorporated by reference herein in its entirety fully as disclosed in the foregoing publication;

Interleukin 1-receptor 1 ("IL1-R1") specific antibodies, peptibodies, and related proteins, and the like, including but not limited to those described in U.S. Publication No. 2004/097712, which is incorporated herein by reference in its entirety in parts pertinent to IL1-R1 specific binding proteins, monoclonal antibodies in particular, especially, without limitation, those designated therein: 15CA, 26F5, 27F2, 24E12, and 10H7, each of which is individually and specifically incorporated by reference herein in its entirety fully as disclosed in the aforementioned publication;

Ang2 specific antibodies, peptibodies, and related proteins, and the like, including but not limited to those described in PCT Publication No. WO 03/057134 and U.S. Publication No. 2003/0229023, each of which is incorporated herein by reference in its entirety particularly in parts pertinent to Ang2 specific antibodies and peptibodies and the like, especially those of sequences described therein and including but not limited to: L1(N); L1(N) WT; L1(N) 1K WT; 2xL1(N); 2xL1(N) WT; Con4 (N), Con4 (N) 1K WT, 2xCon4 (N) 1K; L1C; L1C 1K; 2xL1C; Con4C; Con4C 1K; 2xCon4C 1K; Con4-L1 (N); Con4-L1C; TN-12-9 (N); C17 (N); TN8-8(N); TN8-14 (N); Con 1 (N), also including anti-Ang 2 antibodies and formulations such as those described in PCT Publication No. WO 2003/030833 which is incorporated herein by reference in its entirety as to the same, particularly Ab526; Ab528; Ab531; Ab533; Ab535; Ab536; Ab537; Ab540; Ab543; Ab544; Ab545; Ab546; A551; Ab553; Ab555; Ab558; Ab559; Ab565; AbF1AbFD; AbFE; AbFJ; AbFK; AbG1D4; AbGC1E8; AbH1C12; AbIA1; AbIF; AbIK, AbIP; and AbIP, in their various permutations as described therein, each of which is individually and specifically incorporated by reference herein in its entirety fully as disclosed in the foregoing publication;

NGF specific antibodies, peptibodies, and related proteins, and the like including, in particular, but not limited to those described in U.S. Publication No. 2005/0074821 and U.S. Pat. No. 6,919,426, which are incorporated herein by reference in their entirety particularly as to NGF-specific antibodies and related proteins in this regard, including in particular, but not limited to, the NGF-specific antibodies therein designated 4D4, 4G6, 6H9, 7H2, 14D10 and 14D11, each of which is individually and specifically incorporated by reference herein in its entirety fully as disclosed in the foregoing publication;

CD22 specific antibodies, peptibodies, and related proteins, and the like, such as those described in U.S. Pat. No. 5,789,554, which is incorporated herein by reference in its entirety as to CD22 specific antibodies and related proteins, particularly human CD22 specific antibodies, such as but not limited to humanized and fully human antibodies, including but not limited to humanized and fully human monoclonal antibodies, particularly including but not limited to human CD22 specific IgG antibodies, such as, for instance, a dimer of a human-mouse monoclonal hLL2 gamma-chain disulfide linked to a human-mouse monoclonal hLL2 kappa-chain, including, but limited to, for example, the human CD22 specific fully humanized antibody in Epratuzumab, CAS registry number 501423-23-0;

IGF-1 receptor specific antibodies, peptibodies, and related proteins, and the like, such as those described in PCT Publication No. WO 06/069202, which is incorporated herein by reference in its entirety as to IGF-1 receptor specific antibodies and related proteins, including but not limited to the IGF-1 specific antibodies therein designated L1H1, L2H2, L3H3, L4H4, L5H5, L6H6, L7H7, L8H8, L9H9, L10H10, L11H11, L12H12, L13H13, L14H14, L15H15, L16H16, L17H17, L18H18, L19H19, L20H20, L21H21, L22H22, L23H23, L24H24, L25H25, L26H26, L27H27, L28H28, L29H29, L30H30, L31H31, L32H32, L33H33, L34H34, L35H35, L36H36, L37H37, L38H38, L39H39, L40H40, L41H41, L42H42, L43H43, L44H44, L45H45, L46H46, L47H47, L48H48, L49H49, L50H50, L51H51, L52H52, and IGF-1R-binding fragments and derivatives thereof, each of which is individually and specifically incorporated by reference herein in its entirety fully as disclosed in the foregoing publication;

Also among non-limiting examples of anti-IGF-1R antibodies for use in the methods and compositions of the present invention are each and all of those described in:

(i) U.S. Publication No. 2006/0040358 (published Feb. 23, 2006), 2005/0008642 (published Jan. 13, 2005), 2004/0228859 (published Nov. 18, 2004), including but not limited to, for instance, antibody 1A (DSMZ Deposit No. DSM ACC 2586), antibody 8 (DSMZ Deposit No. DSM ACC 2589), antibody 23 (DSMZ Deposit No. DSM ACC 2588) and antibody 18 as described therein;

(ii) PCT Publication No. WO 06/138729 (published Dec. 28, 2006) and WO 05/016970 (published Feb. 24, 2005), and Lu et al. (2004), J. Biol. Chem. 279:2856-2865, including but not limited to antibodies 2F8, A12, and IMC-A12 as described therein;

(iii) PCT Publication No. WO 07/012614 (published Feb. 1, 2007), WO 07/000328 (published Jan. 4, 2007), WO 06/013472 (published Feb. 9, 2006), WO 05/058967 (published Jun. 30, 2005), and WO 03/059951 (published Jul. 24, 2003);

(iv) U.S. Publication No. 2005/0084906 (published Apr. 21, 2005), including but not limited to antibody 7C10, chimaeric antibody C7C10, antibody h7C10, antibody 7H2M, chimaeric antibody *7C10, antibody GM 607, humanized antibody 7C10 version 1, humanized antibody 7C10 version 2, humanized antibody 7C10 version 3, and antibody 7H2HM, as described therein;

(v) U.S. Publication Nos. 2005/0249728 (published Nov. 10, 2005), 2005/0186203 (published Aug. 25, 2005), 2004/0265307 (published Dec. 30, 2004), and 2003/0235582 (published Dec. 25, 2003) and Maloney et al. (2003), Cancer Res. 63:5073-5083, including but not limited to antibody EM164, resurfaced EM164, humanized EM164, huEM164 v1.0, huEM164 v1.1, huEM164 v1.2, and huEM164 v1.3 as described therein;

(vi) U.S. Pat. No. 7,037,498 (issued May 2, 2006), U.S. Publication Nos. 2005/0244408 (published Nov. 30, 2005) and 2004/0086503 (published May 6, 2004), and Cohen, et al. (2005), Clinical Cancer Res. 11:2063-2073, e.g., antibody CP-751,871, including but not limited to each of the antibodies produced by the hybridomas having the ATCC accession numbers PTA-2792, PTA-2788, PTA-2790, PTA-2791, PTA-2789, PTA-2793, and antibodies 2.12.1, 2.13.2, 2.14.3, 3.1.1, 4.9.2, and 4.17.3, as described therein;

(vii) U.S. Publication Nos. 2005/0136063 (published Jun. 23, 2005) and 2004/0018191 (published Jan. 29, 2004), including but not limited to antibody 19D12 and an antibody comprising a heavy chain encoded by a polynucleotide in plasmid 15H12/19D12HCA (γ4), deposited at the ATCC under number PTA-5214, and a light chain encoded by a polynucleotide in plasmid 15H12/19D12 LCF (κ), deposited at the ATCC under number PTA-5220, as described therein; and (viii) U.S. Publication No. 2004/0202655 (published Oct. 14, 2004), including but not limited to antibodies PINT-6A1, PINT-7A2, PINT-7A4, PINT-7A5, PINT-7A6, PINT-8A1, PINT-9A2, PINT-11A1, PINT-11A2, PINT-11A3, PINT-11A4, PINT-11A5, PINT-11A7, PINT-11A12, PINT-12A1, PINT-12A2, PINT-12A3, PINT-12A4, and PINT-12A5, as described therein; each and all of which are herein incorporated by reference in their entireties, particularly as to the aforementioned antibodies, peptibodies, and related proteins and the like that target IGF-1 receptors;

B-7 related protein 1 specific antibodies, peptibodies, related proteins and the like ("B7RP-1," also is referred to in the literature as B7H2, ICOSL, B7h, and CD275), particularly B7RP-specific fully human monoclonal IgG2 antibodies, particularly fully human IgG2 monoclonal antibody that binds an epitope in the first immunoglobulin-like domain of B7RP-1, especially those that inhibit the interaction of B7RP-1 with its natural receptor, ICOS, on activated T cells in particular, especially, in all of the foregoing regards, those disclosed in U.S. Publication No. 2008/0166352 and PCT Publication No. WO 07/011941, which are incorporated herein by reference in their entireties as to such antibodies and related proteins, including but not limited to antibodies designated therein as follow: 16H (having light chain variable and heavy chain variable sequences SEQ ID NO:1 and SEQ ID NO:7 respectively therein); 5D (having light chain variable and heavy chain variable sequences SEQ ID NO:2 and SEQ ID NO:9 respectively therein); 2H (having light chain variable and heavy chain variable sequences SEQ ID NO:3 and SEQ ID NO:10 respectively therein); 43H (having light chain variable and heavy chain variable sequences SEQ ID NO:6 and SEQ ID NO:14 respectively therein); 41H (having light chain variable and heavy chain variable sequences SEQ ID NO:5 and SEQ ID NO:13 respectively therein); and 15H (having light chain variable and heavy chain variable sequences SEQ ID NO:4 and SEQ ID NO:12 respectively therein), each of which is individually and specifically incorporated by reference herein in its entirety fully as disclosed in the foregoing publication;

IL-15 specific antibodies, peptibodies, and related proteins, and the like, such as, in particular, humanized monoclonal antibodies, particularly antibodies such as those disclosed in U.S. Publication Nos. 2003/0138421; 2003/023586; and 2004/0071702; and U.S. Pat. No. 7,153,507, each of which is incorporated herein by reference in its entirety as to IL-15 specific antibodies and related proteins, including peptibodies, including particularly, for instance, but not limited to, HuMax IL-15 antibodies and related proteins, such as, for instance, 146B7;

IFN gamma specific antibodies, peptibodies, and related proteins and the like, especially human IFN gamma specific antibodies, particularly fully human anti-IFN gamma antibodies, such as, for instance, those described in U.S. Publication No. 2005/0004353, which is incorporated herein by reference in its entirety as to IFN gamma specific antibodies, particularly, for example, the antibodies therein designated 1118; 1118*; 1119; 1121; and 1121*. The entire sequences of the heavy and light chains of each of these antibodies, as well as the sequences of their heavy and light chain variable regions and complementarity determining regions, are each individually and specifically incorporated by reference herein in its entirety fully as disclosed in the foregoing publication and in Thakur et al. (1999), Mol. Immunol. 36:1107-1115. In addition, description of the properties of these antibodies provided in the foregoing publication is also incorporated by reference herein in its entirety. Specific antibodies include those having the heavy chain of SEQ ID NO:17 and the light chain of SEQ ID NO:18; those having the heavy chain variable region of SEQ ID NO:6 and the light chain variable region of SEQ ID NO:8; those having the heavy chain of SEQ ID NO:19 and the light chain of SEQ ID NO:20; those having the heavy chain variable region of SEQ ID NO:10 and the light chain variable region of SEQ ID NO:12; those having the heavy chain of SEQ ID NO:32 and the light chain of SEQ ID NO:20; those having the heavy chain variable region of SEQ ID NO:30 and the light chain variable region of SEQ ID NO:12; those having the heavy chain sequence of SEQ ID NO:21 and the light chain sequence of SEQ ID NO:22; those having the heavy chain variable region of SEQ ID NO:14 and the light chain variable region of SEQ ID NO:16; those having the heavy chain of SEQ ID NO:21 and the light chain of SEQ ID NO:33; and those having the heavy chain variable region of SEQ ID NO:14 and the light chain variable region of SEQ ID NO:31, as disclosed in the foregoing publication. A specific antibody contemplated is antibody 1119 as disclosed in the foregoing U.S. publication and having a complete heavy chain of SEQ ID NO:17 as disclosed therein and having a complete light chain of SEQ ID NO:18 as disclosed therein;

TALL-1 specific antibodies, peptibodies, and the related proteins, and the like, and other TALL specific binding proteins, such as those described in U.S. Publication Nos. 2003/0195156 and 2006/0135431, each of which is incorporated herein by reference in its entirety as to TALL-1 binding proteins, particularly the molecules of Tables 4 and 5B, each of which is individually and specifically incorporated by reference herein in its entirety fully as disclosed in the foregoing publications;

Parathyroid hormone ("PTH") specific antibodies, peptibodies, and related proteins, and the like, such as those described in U.S. Pat. No. 6,756,480, which is incorporated herein by reference in its entirety, particularly in parts pertinent to proteins that bind PTH;

Thrombopoietin receptor ("TPO-R") specific antibodies, peptibodies, and related proteins, and the like, such as those described in U.S. Pat. No. 6,835,809, which is herein incorporated by reference in its entirety, particularly in parts pertinent to proteins that bind TPO-R;

Hepatocyte growth factor ("HGF") specific antibodies, peptibodies, and related proteins, and the like, including those that target the HGF/SF:cMet axis (HGF/SF:c-Met), such as the fully human monoclonal antibodies that neutralize hepatocyte growth factor/scatter (HGF/SF) described in U.S. Publication No. 2005/0118643 and PCT Publication No. WO 2005/017107, huL2G7 described in U.S. Pat. No. 7,220,410 and OA-5d5 described in U.S. Pat. Nos. 5,686,292 and 6,468,529 and in PCT Publication No. WO 96/38557, each of which is incorporated herein by reference in its entirety, particularly in parts pertinent to proteins that bind HGF;

TRAIL-R2 specific antibodies, peptibodies, related proteins and the like, such as those described in U.S. Pat. No. 7,521,048, which is herein incorporated by reference in its entirety, particularly in parts pertinent to proteins that bind TRAIL-R2;

Activin A specific antibodies, peptibodies, related proteins, and the like, including but not limited to those described in U.S. Publication No. 2009/0234106, which is herein incorporated by reference in its entirety, particularly in parts pertinent to proteins that bind Activin A;

TGF-beta specific antibodies, peptibodies, related proteins, and the like, including but not limited to those described in U.S. Pat. No. 6,803,453 and U.S. Publication No. 2007/0110747, each of which is herein incorporated by reference in its entirety, particularly in parts pertinent to proteins that bind TGF-beta;

Amyloid-beta protein specific antibodies, peptibodies, related proteins, and the like, including but not limited to those described in PCT Publication No. WO 2006/081171, which is herein incorporated by reference in its entirety, particularly in parts pertinent to proteins that bind amyloid-beta proteins. One antibody contemplated is an antibody having a heavy chain variable region comprising SEQ ID NO:8 and a light chain variable region having SEQ ID NO:6 as disclosed in the foregoing publication;

c-Kit specific antibodies, peptibodies, related proteins, and the like, including but not limited to those described in U.S. Publication No. 2007/0253951, which is incorporated herein by reference in its entirety, particularly in parts pertinent to proteins that bind c-Kit and/or other stem cell factor receptors;

OX40L specific antibodies, peptibodies, related proteins, and the like, including but not limited to those described in U.S. Publication No. 2006/0002929, which is incorporated herein by reference in its entirety, particularly in parts pertinent to proteins that bind OX40L and/or other ligands of the OX40 receptor; and Other exemplary proteins, including Activase® (alteplase, tPA); Aranesp® (darbepoetin alfa); Epogen® (epoetin alfa, or erythropoietin); GLP-1, Avonex® (interferon beta-1a); Bexxar® (tositumomab, anti-CD22 monoclonal antibody); Betaseron® (interferon-beta); Campath® (alemtuzumab, anti-CD52 monoclonal antibody); Dynepo® (epoetin delta); Velcade® (bortezomib); MLN0002 (anti-α4β7 mAb); MLN1202 (anti-CCR2 chemokine receptor mAb); Enbrel® (etanercept, TNF-receptor/Fc fusion protein, TNF blocker); Eprex® (epoetin alfa); Erbitux® (cetuximab, anti-EGFR/HER1/c-ErbB-1); Genotropin® (somatropin, Human Growth Hormone); Herceptin® (trastuzumab, anti-HER2/neu (erbB2) receptor mAb); Humatrope® (somatropin, Human Growth Hormone); Humira® (adalimumab); insulin in solution; Infergen® (interferon alfacon-1); Natrecor® (nesiritide; recombinant human B-type natriuretic peptide (hBNP); Kineret® (anakinra); Leukine® (sargamostim, rhuGM-CSF); LymphoCide® (epratuzumab, anti-CD22 mAb); Benlysta™ (lymphostat B, belimumab, anti-BlyS mAb); Metalyse® (tenecteplase, t-PA analog); Mircera® (methoxy polyethylene glycol-epoetin beta); Mylotarg® (gemtuzumab ozogamicin); Raptiva® (efalizumab); Cimzia® (certolizumab pegol, CDP 870); Soliris™ (eculizumab); pexelizumab (anti-C5 complement); Numax® (MEDI-524); Lucentis® (ranibizumab); Panorex® (17-1A, edrecolomab); Trabio® (lerdelimumab); TheraCim hR3 (nimotuzumab); Omnitarg (pertuzumab, 2C4); Osidem® (IDM-1); OvaRex® (B43.13); Nuvion® (visilizumab); cantuzumab mertansine (huC242-DM1); NeoRecormon® (epoetin beta); Neumega® (oprelvekin, human interleukin-11); Neulasta® (pegylated filgastrim, pegylated G-CSF, pegylated hu-Met-G-CSF); Neupogen® (filgrastim, G-CSF, hu-MetG-CSF); Orthoclone OKT3® (muromonab-CD3, anti-CD3 monoclonal antibody); Procrit® (epoetin alfa); Remicade® (infliximab, anti-TNFα monoclonal antibody); Reopro® (abciximab, anti-GP IIb/IIIa receptor monoclonal antibody); Actemra® (anti-IL6 Receptor mAb); Avastin® (bevacizumab), HuMax-CD4 (zanolimumab); Rituxan® (rituximab, anti-CD20 mAb); Tarceva® (erlotinib); Roferon-A®-(interferon alfa-2a); Simulect® (basiliximab); Prexige® (lumiracoxib); Synagis® (palivizumab); 146B7-CHO (anti-IL15 antibody, see U.S. Pat. No. 7,153,507); Tysabri® (natalizumab, anti- α4integrin mAb); Valortim® (MDX-1303, anti-*B. anthracis* protective antigen mAb); ABthrax™; Vectibix® (panitumumab); Xolair® (omalizumab); ETI211 (anti-MRSA mAb); IL-1 trap (the Fc portion of human IgG1 and the extracellular domains of both IL-1 receptor components (the Type I receptor and receptor accessory protein)); VEGF trap (Ig domains of VEGFR1 fused to IgG1 Fc); Zenapax® (daclizumab); Zenapax® (daclizumab, anti-IL-2Rα mAb); Zevalin® (ibritumomab tiuxetan); Zetia® (ezetimibe); Orencia® (atacicept, TACI-Ig); anti-CD80 monoclonal antibody (galiximab); anti-CD23 mAb (lumiliximab); BR2-Fc (huBR3/huFc fusion protein, soluble BAFF antagonist); CNTO 148 (golimumab, anti-TNFα mAb); HGS-ETR1 (mapatumumab; human anti-TRAIL Receptor-1 mAb); HuMax-CD20 (ocrelizumab, anti-CD20 human mAb); HuMax-EGFR (zalutumumab); M200 (volociximab, anti-α5β1 integrin mAb); MDX-010 (ipilimumab, anti-CTLA-4 mAb and VEGFR-1 (IMC-18F1); anti-BR3 mAb; anti-*C. difficile* Toxin A and Toxin B C mAbs MDX-066 (CDA-1) and MDX-1388); anti-CD22 dsFv-PE38 conjugates (CAT-3888 and CAT-8015); anti-CD25 mAb (HuMax-TAC); anti-CD3 mAb (NI-0401); adecatumumab; anti-CD30 mAb (MDX-060); MDX-1333 (anti-IFNAR); anti-CD38 mAb (HuMax CD38); anti-CD40L mAb; anti-Cripto mAb; anti-CTGF Idiopathic Pulmonary Fibrosis Phase I Fibrogen (FG-3019); anti-CTLA4 mAb; anti-eotaxin1 mAb (CAT-213); anti-FGF8 mAb; anti-ganglioside GD2 mAb; anti-ganglioside GM2 mAb; anti-GDF-8 human mAb (MYO-029); anti-GM-CSF Receptor mAb (CAM-3001); anti-HepC mAb (HuMax HepC); anti-IFNα mAb (MEDI-545, MDX-1103); anti-IGF1R mAb; anti-IGF-1R mAb (HuMax-Inflam); anti-IL12 mAb (ABT-874); anti-IL12/IL23 mAb (ONTO 1275); anti-IL13 mAb (CAT-354); anti-IL2Ra mAb (HuMax-TAC); anti-IL5 Receptor mAb; anti-integrin receptors mAb (MDX-018, ONTO 95); anti-IP10 Ulcerative Colitis mAb (MDX-1100); anti-LLY antibody; BMS-66513; anti-Mannose Receptor/hCGβ mAb (MDX-1307); anti-mesothelin dsFv-PE38 conjugate (CAT-5001); anti-PD1 mAb (MDX-1106 (ONO-4538)); anti-PDGFRa antibody (IMC-3G3); anti-TGFß mAb (GC-1008); anti-TRAIL Receptor-2 human mAb (HGS-ETR2); anti-TWEAK mAb; anti-VEGFR/Flt-1 mAb; anti-ZP3 mAb (HuMax-ZP3); NVS Antibody #1; and NVS Antibody #2.

Also included can be a sclerostin antibody, such as but not limited to romosozumab, blosozumab, or BPS 804 (Novartis). Further included can be therapeutics such as rilotumumab, bixalomer, trebananib, ganitumab, conatumumab, motesanib diphosphate, brodalumab, vidupiprant, panitumumab, denosumab, NPLATE, PROLIA, VECTIBIX or XGEVA. Additionally, included in the device can be a monoclonal antibody (IgG) that binds human Proprotein Convertase Subtilisin/Kexin Type 9 (PCSK9). Such PCSK9 specific antibodies include, but are not limited to, Repatha® (evolocumab) and Praluent® (alirocumab), as well as molecules, variants, analogs or derivatives thereof as disclosed in the following patents or patent applications, each of which is herein incorporated by reference in its entirety for all purposes: U.S. Pat. No. 8,030,547, U.S. Publication No. 2013/0064825, WO2008/057457, WO2008/057458, WO2008/057459, WO2008/063382, WO2008/133647, WO2009/100297, WO2009/100318, WO2011/037791, WO2011/053759, WO2011/053783, WO2008/125623, WO2011/072263, WO2009/055783, WO2012/0544438, WO2010/029513, WO2011/111007, WO2010/077854, WO2012/088313, WO2012/101251, WO2012/101252, WO2012/101253, WO2012/109530, and WO2001/031007.

Also included can be talimogene laherparepvec or another oncolytic HSV for the treatment of melanoma or other cancers. Examples of oncolytic HSV include, but are not limited to talimogene laherparepvec (U.S. Pat. Nos. 7,223,593 and 7,537,924); OncoVEXGALV/CD (U.S. Pat. No. 7,981,669); OrienX010 (Lei et al. (2013), World J. Gastroenterol., 19:5138-5143); G207, 1716; NV1020; NV12023; NV1034 and NV1042 (Vargehes et al. (2002), Cancer Gene Ther., 9(12):967-978).

Also included are TIMPs. TIMPs are endogenous tissue inhibitors of metalloproteinases (TIMPs) and are important in many natural processes. TIMP-3 is expressed by various cells or and is present in the extracellular matrix; it inhibits all the major cartilage-degrading metalloproteases, and may play a role in role in many degradative diseases of connective tissue, including rheumatoid arthritis and osteoarthritis, as well as in cancer and cardiovascular conditions. The amino acid sequence of TIMP-3, and the nucleic acid sequence of a DNA that encodes TIMP-3, are disclosed in U.S. Pat. No. 6,562,596, issued May 13, 2003, the disclosure of which is incorporated by reference herein. Description of TIMP mutations can be found in U.S. Publication No. 2014/0274874 and PCT Publication No. WO 2014/152012.

Also included are antagonistic antibodies for human calcitonin gene-related peptide (CGRP) receptor and bispecific antibody molecule that target the CGRP receptor and other headache targets. Further information concerning these molecules can be found in PCT Application No. WO 2010/075238.

Additionally, bispecific T cell engager (BiTE®) antibodies, e.g. BLINCYTO® (blinatumomab), can be used in the device. Alternatively, included can be an APJ large molecule agonist e.g., apelin or analogues thereof in the device. Information relating to such molecules can be found in PCT Publication No. WO 2014/099984.

In certain embodiments, the medicament comprises a therapeutically effective amount of an anti-thymic stromal lymphopoietin (TSLP) or TSLP receptor antibody. Examples of anti-TSLP antibodies that may be used in such embodiments include, but are not limited to, those described in U.S. Pat. Nos. 7,982,016, and 8,232,372, and U.S. Publication No. 2009/0186022. Examples of anti-TSLP receptor antibodies include, but are not limited to, those described in U.S. Pat. No. 8,101,182. In particularly preferred embodiments, the medicament comprises a therapeutically effective amount of the anti-TSLP antibody designated as A5 within U.S. Pat. No. 7,982,016.

Although the modular fluid path assemblies, drug delivery devices, methods, and components thereof, have been described in terms of exemplary embodiments, they are not limited thereto. The detailed description is to be construed as exemplary only and does not describe every possible embodiment of the invention because describing every possible embodiment would be impractical, if not impossible. Numerous alternative embodiments could be implemented, using either current technology or technology developed after the filing date of this patent that would still fall within the scope of the claims defining the invention. For example, while the modular fluid path assemblies are described herein with reference to on-body injector drug delivery devices, the assemblies can also be utilized in other drug delivery devices, such as autoinjector drug delivery devices.

It should be understood that the legal scope of the invention is defined by the words of the claims set forth at the end of this patent. The appended claims should be construed broadly to include other variants and embodiments of same, which may be made by those skilled in the art without departing from the scope and range of equivalents of the modular fluid path assemblies, drug delivery devices, methods, and their components.

Those skilled in the art will recognize that a wide variety of modifications, alterations, and combinations can be made with respect to the above described embodiments without departing from the scope of the invention, and that such modifications, alterations, and combinations are to be viewed as being within the ambit of the inventive concept.

What is claimed is:

1. A modular fluid path assembly for a drug delivery device, the modular fluid path assembly comprising: a container having an interior for storing a medicament and an outlet; a conduit portion of a fluid path fluidly coupled to the outlet of the container; a coupling portion of the fluid path configured to snap-fit to a needle insertion mechanism to thereby couple the fluid path to the needle insertion mechanism, the coupling portion fluidly coupled to the conduit portion; a needle of the fluid path fluidly coupled to the coupling portion, wherein the needle is configured to be inserted into a user by the needle insertion mechanism; and a needle shield having a tip of the needle embedded therein.

2. The modular fluid path assembly of claim 1, further comprising:
the medicament disposed within the container; and
a stopper sealingly disposed within the interior of the container.

3. The modular fluid path assembly of claim 1, wherein the coupling portion comprises a hub having the needle mounted thereto, the hub configured to snap-fit to the needle insertion mechanism.

4. The modular fluid path assembly of claim 3, wherein the hub and needle insertion mechanism comprises a tongue and groove cooperating structure.

5. The modular fluid path assembly of claim 1, further comprising a cannula of the fluid path, the cannula configured to operably couple to the needle insertion mechanism to be driven thereby.

6. The modular fluid path assembly of claim 3 in combination with the needle insertion mechanism, wherein the needle insertion mechanism comprises a scotch yoke mechanism, and the hub comprises a yoke member of the scotch yoke mechanism or mounts to a yoke member of the scotch yoke mechanism.

7. A method preparing a modular fluid path assembly for a drug delivery device, the method comprising: providing a container having an interior for storing a medicament and an outlet; coupling a conduit portion of a fluid path to an outlet of the container, the fluid path further including a coupling portion configured to snap-fit to a needle insertion mechanism to thereby couple the fluid path to the needle insertion mechanism, and a needle fluidly coupled to the coupling portion and configured to be inserted into a user by the needle insertion mechanism; embedding a tip of the needle in a needle shield; sterilizing the container, conduit, coupling portion, needle, and needle shield; dispensing a medicament into the container; and inserting a stopper into the interior of the container.

8. The method of claim 7, further comprising installing the modular fluid path assembly in a drug delivery device, wherein installing the modular fluid path assembly in the drug delivery device comprises:
operably coupling the coupling portion of the fluid path to the needle insertion mechanism of the drug delivery device; and
aligning the container with a plunger drive mechanism of the drug delivery device.

9. The method of claim 8, wherein the coupling portion comprises a hub having the needle mounted thereto, and operably coupling the coupling portion of the fluid path to the needle insertion mechanism comprises inserting mounting structure of the hub into a slot opening of the needle insertion mechanism to thereby snap-fit the hub to the needle insertion mechanism.

10. The method of claim 9, wherein the needle insertion mechanism comprises a scotch yoke mechanism and inserting the portion of the hub into the slot opening of the needle insertion mechanism further comprises coupling the hub to a drive pin of the scotch yoke mechanism.

11. A method preparing a drug delivery device with a modular fluid path assembly, the method comprising: providing a container having an interior for storing a medicament and an outlet; coupling a conduit portion of a fluid path to an outlet of the container, the fluid path further including a coupling portion comprising a hub, and a needle fluidly coupled to the coupling portion; embedding a tip of the needle in a needle shield; dispensing a medicament into the container; inserting a stopper into the interior of the container; and installing the modular fluid path assembly in the drug delivery device, wherein installing the modular fluid path assembly in the drug delivery device comprises: operably coupling the coupling portion of the fluid path to a needle insertion mechanism of the drug delivery device by inserting mounting structure of the hub into a slot opening of the needle insertion mechanism, such that the needle is configured to be inserted into a user by the needle insertion mechanism; and aligning the container with a plunger drive mechanism of the drug delivery device.

12. The method of claim 11, wherein the needle insertion mechanism comprises a scotch yoke mechanism and inserting the portion of the hub into the slot opening of the needle insertion mechanism further comprises coupling the hub to a drive pin of the scotch yoke mechanism.

* * * * *